US006917663B2

(12) United States Patent
Taguchi et al.

(10) Patent No.: US 6,917,663 B2
(45) Date of Patent: Jul. 12, 2005

(54) CONE-BEAM RECONSTRUCTION APPARATUS AND COMPUTED TOMOGRAPHY APPARATUS

(75) Inventors: Katsuyuki Taguchi, Buffalo Grove, IL (US); Be-Shan Su Chiang, Buffalo Grove, IL (US)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/461,401

(22) Filed: Jun. 16, 2003

(65) Prior Publication Data

US 2004/0252806 A1 Dec. 16, 2004

(51) Int. Cl.[7] .................................. A61B 6/03
(52) U.S. Cl. ........................ 378/8; 378/15; 378/901
(58) Field of Search ................ 378/4, 8, 15, 19, 378/901

(56) References Cited

U.S. PATENT DOCUMENTS

| | | | |
|---|---|---|---|
| 5,708,691 A | 1/1998 | Zmora | 378/4 |
| 5,825,842 A | 10/1998 | Taguchi | 378/15 |
| 6,324,241 B1 * | 11/2001 | Besson | 378/4 |
| 6,341,154 B1 * | 1/2002 | Besson | 378/15 |

OTHER PUBLICATIONS

G.E. Medical Systems, "LightSpeed Image Reconstruction," (Jul. 2002).
Jiang Hsieh, Brian Grekowicz, Piero Simoni, et al., "Convolution Reconstruction Algorithm for Multi–slice Helical CT," SPIE vol. 5032 (2003), Medical Imaging 2003, pp. 716–723.

* cited by examiner

*Primary Examiner*—David V Bruce
(74) *Attorney, Agent, or Firm*—Oblon, Spivak, McClelland, Maier & Neustadt, P.C.

(57) ABSTRACT

A method for obtaining data from CT scans, including obtaining projection data from at least one detector row in a CT system; applying a weighting function including cone-angle dependent weight to projection data; filtering weighted data; and backprojecting weighted data while accounting for cone-angle. The method finds application to an X-ray CT apparatus, including a helical scanning device configured to collect projection data while at least one of a gantry and a couch moves along an axial direction, the helical scanning device including an X-ray source to generate X-rays, and a detector having detector elements arranged in rows along the axial direction to produce projection data; and a processor, which includes a weighting device to apply a weighting function including cone-angle dependent weight to projection data, thereby obtaining weighted data, a filtering device to filter weighted data, and a backprojecting device to backproject weighted data while accounting for cone-angle.

19 Claims, 46 Drawing Sheets

US 6,917,663 B2

CONE-BEAM RECONSTRUCTION APPARATUS AND COMPUTED TOMOGRAPHY APPARATUS

BACKGROUND OF THE INVENTION

Field of the Invention

Multi-slice X-ray computed tomography (CT) systems were developed and introduced into the medical market in 1998. Generally, the number of slices used in a multi-slice X-ray CT ranges from about 2 to about 16. However, the number of slices is expected to increase. Some expect the number of slices used to increase to 32, 64, or even perhaps 256. (See references Y. Saito, H. Aradate, H. Miyazaki, K. Igarashi, and H. Ide, "Development of a large area 2-dimensional detector for real-time 3-dimensional CT (4D-CT)," *Radiology* vol. 217(P), 405 (2000); Y. Saito, H. Aradate, H. Miyazaki, K. Igarashi, and H. Ide, "Large area two-dimensional detector system for real-time three-dimensional CT (4D-CT)," *Proc. of SPIE Med. Imag. Conf.,* 4320, 775–782 (2001); and http://www3.toshiba.co.jp/medical/4d-ct/, and the contents of each are herein incorporated by reference).

Several imagery construction algorithms are used for helical scanning in a multi-slice X-ray CT system. One such image reconstruction algorithm uses a generalized weighted version of a Feldkamp reconstruction algorithm. (See L. A. Feldkamp, L. C. Davis, and J. W. Kress, "Practical cone-beam algorithm," *J. Opt. Soc. Am. A,* 6, 612–19 (1984); H. Aradate and K. Nambu, "Computed tomography apparatus," Japanese Patent No. 2,825,352; L. G. Zeng and G. T. Gullberg, "Short-scan cone beam algorithm for circular and noncircular detector orbit," *Proc. of SPIE Med. Imag. Conf,* 1233, 453–463 (1990); H. Kudo and T. Saito, "Three-dimensional helical-scan computed tomography using cone-beam projections," *J. Electron. Information Commun. Soc. Japan*, J74-D-II, 1108–1114 (1991); G. Wang, T. H. Lin, P. C. Cheng, D. M. Shinozaki, "A general cone-beam reconstruction algorithm," *IEEE Trans. Med. Imaging,* 12, 486–496 (1993); K. Taguchi, "X-ray computed tomography apparatus," U.S. Pat. No. 5,825,842 (Filed in 1995); K. Wiesent, K. Barth, N. Novab, et al., "Enhanced 3-D-reconstruction algorithm for C-arm systems suitable for interventional procedures," *IEEE Trans. Med. Imaging,* 19, 391–403 (2000); M. D. Silver, K. Taguchi, and K. S. Han, "Field-of-view dependent helical pitch in multi-slice CT," *Proc. of SPIE Med. Imag. Conf.,* 4320, 839–850 (2001); M. D. Silver, K. Taguchi, and I. A. Hein, "A simple algorithm for increased helical pitch in cone-beam CT," *The Sixth International Meeting on Fully Three-Dimensional Image Reconstruction in Radiology and Nuclear Medicine,* 70–73 (2001), and the contents of each are herein incorporated by reference). The generalized weighted version of the Feldkamp reconstruction algorithm introduces a flexible focus orbit and applies a weighting function to the Feldkamp algorithm. Specifically, the algorithm applies weight to projection data prior to 1-dimensional (1D) filtering (or convolution) and 3-dimensional (3D) backprojection.

The weighting function may be one developed for 2-dimensional (2D) fan-beam reconstruction. Using the weighting function developed for 2D fan-beam reconstruction, however, the same weight is applied to all detector rows. In other words, weight is independent of cone-angle, even though the projection data in the cone-beam CT is diversion in detector row (z) direction with cone-angle.

As the number of examinations using multi-slice CT increases, the X-ray exposure in CT scanning has become more of a concern. As a result, physicians and physicists have increased their efforts to reduce the patient dose while keeping an image noise constant. Additionally, physicists and physicians seek to decrease the image noise using the same data.

SUMMARY OF THE INVENTION

Accordingly, an object of this invention is to provide a method, system, and computer program product for improved multi-slice X-ray computer tomography systems using a detector row dependent weight to the generalized weighted cone-beam backprojection. One example of a backprojection technique to which the invention is particularly applicable is the helical Feldkamp algorithm. Some useful techniques of Feldkamp reconstruction may be found in (L. A. Feldkamp, L. C. Davis, and J. W. Kress, "Practical Cone-Beam Algorithm," *Journal Optical Society of America*, Vol. 1, pp 612–619 (1984), the contents of which are incorporated herein by reference).

This and other objects are achieved by a way of a method, system, and computer program product constructed according to the present invention, wherein the detector row dependent weight is applied to the generalized weighted cone-beam backprojection, such as a helical Feldkamp algorithm. Thereby, the projection data range is increased without sacrificing image quality (without introducing additional artifacts). Through the present invention, it is possible to decrease the image noise from an identical data set. Simply put, it is possible to use noisier data with a smaller patient dose to achieve the same output image.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
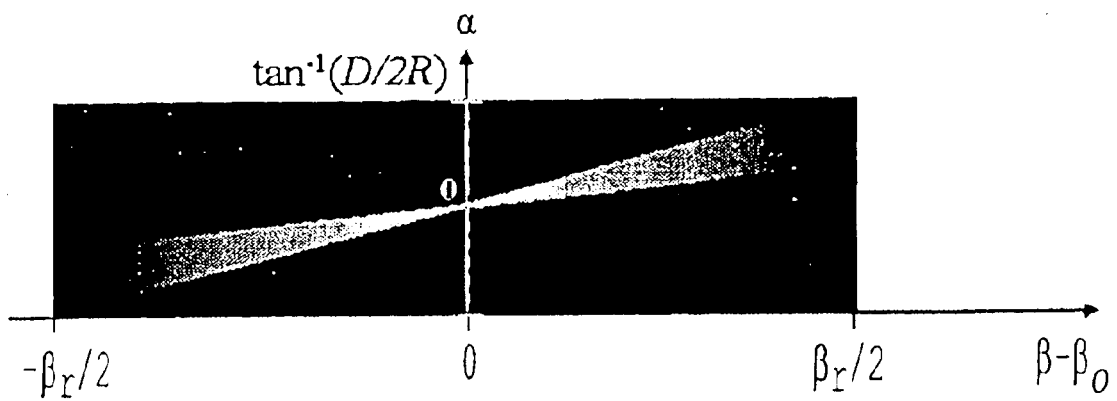
FIG. 1a illustrates an example with the current weight at $\gamma=0$.
Figure 1B:
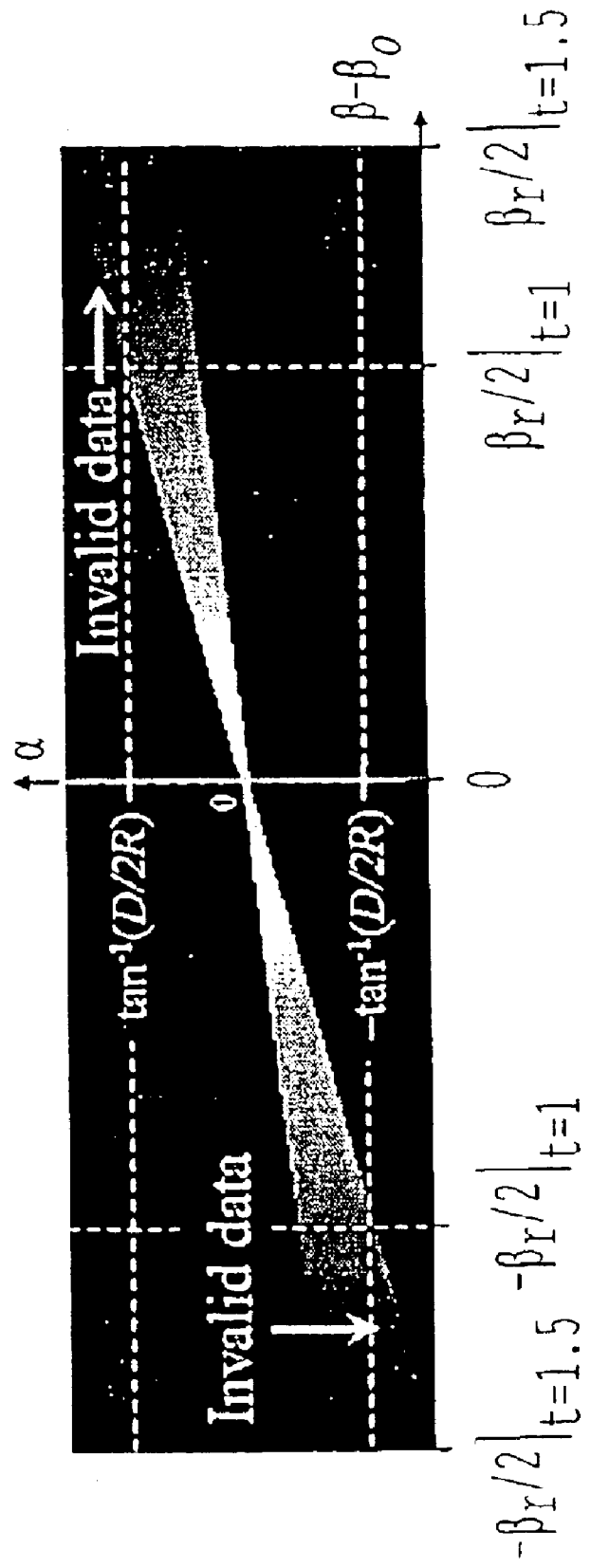
FIG. 1b also illustrates the current weighting method.

Referring now to the drawings, wherein like reference numerals designate identical or corresponding parts throughout the several views, FIG. 1a shows an example of the current weight at $\gamma=0$. One of the problems of using the current weight at $\gamma=0$ is that when the projection angular range (as shown in FIGS. 1a and 1b) is extended, replicated invalid data have the same weight. Using such invalid data degrades image quality by introducing artifacts and increasing noise if an extrapolation method is used.

Figure 1C:
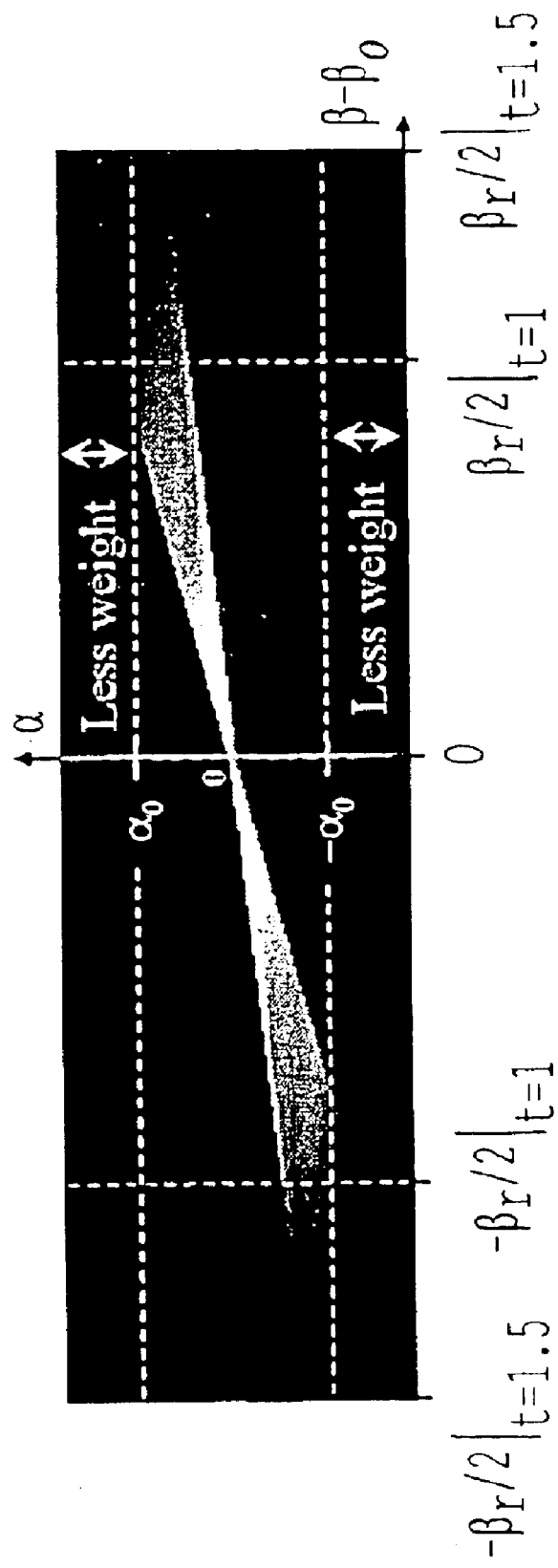
FIG. 1c is illustrative of the weighting method of the present invention.

In light of the deficiencies of the current method, the Applicants have discovered another weighting application as a function of the validity of the projection data. This weighted data is then combined with the overscan or extended half-scan methods, depending on the helical pitch. The newly discovered weighting method permits extension of the projection angular range for reconstruction, while minimizing the side effects of extrapolation or replication, as shown in FIG. 1c.

The following parameters are useful when performing the newly discovered weighting method of the present invention:

$\beta$, $\gamma$, $\alpha$: projection angle, ray angle, and cone angle for direct ray;

$\beta_c$, $\gamma_c$, $\alpha_c$: projection angle, ray angle, and cone angle for complementary ray;

$\gamma_m$, $\Gamma_m$: physical and virtual fan angle;

$\alpha_0$ Tuning parameter-1: cone angle to start decreasing weight;

$\alpha_m$ Tuning parameter-2: $\alpha_0 < \alpha_m$ (width for weighting curve);

a Tuning parameter-3: $0 < a < 1$ (height of weighting curve);

l Table feed per one rotation [mm/rev];

R Focus to rotation axis distance [mm];

r The radius of maximum field of view [mm];

L, $L_c$ Focus to voxel distance projected onto the xy plane; and z, $z_c$ The z coordinate of the focus position.

Generally, cone-beam projections measured along a helical orbit are given by the equations:

$$g(\beta,\gamma,\alpha) = \int f(\vec{s}(\beta) + l\vec{\phi}_{\beta,\gamma,\alpha}) dl \quad (1)$$

$$\vec{s}(\beta) = (R\cos\beta, R\sin\beta, H\cdot\beta/2\pi)^T; \quad 0 \le \beta \le 2\pi n, \quad (2)$$

where $f(\vec{r})$ is the object to reconstruct, R is the radius of the helical orbit, H is the helical pitch, ($\beta$, $\gamma$, $\alpha$) denote projection angle, ray angle, and cone angle, respectively, and $\vec{\phi}_{\beta,\gamma,\alpha}$ denotes the unit vector, which is directed from the x-ray focus $\vec{s}(\beta)$ toward the point ($\gamma$, $\alpha$) on the cylindrical detector surface at $\beta$. Current experiments indicate that combination of $\square_0$ corresponding to slightly inside of the edge and $\square_m$ slightly outside of the edge achieve the best results.

Current Weighted Feldkamp Helical Algorithm

The present embodiment will now be described applying the generalized weighted Feldkamp algorithm. However, other backprojection techniques are equally applicable, and the following description based on the Feldkamp algorithm should not be deemed to preclude the application of the present invention to other techniques of backprojection.

The generalized weighted Feldkamp algorithm includes the following three steps: 1) applying a weighting function to the projection data (applying the same weight to all of the detector rows), 2) filtering the data in the horizontal direction, and 3) cone-beam backprojection.

Step 1: Weighting $$\tilde{g}(\beta,\gamma,\alpha) = \cos\zeta(\gamma,\alpha)\cdot w(\beta-\beta_0,\gamma,\alpha)\cdot g(\beta,\gamma,\alpha), \quad (3)$$

$$\cos\zeta(\gamma,\alpha) = \vec{\phi}_{\beta,\gamma,\alpha}\cdot\vec{\phi}_{\beta,0,0}, \quad (4)$$

where $w(\beta,\gamma,\alpha)$ denotes the weighting function (discussed later) and $\beta_0$ refers to the center of data range used in reconstruction ($\beta_r$).

Steps 2 and 3: Filtering and Cone-Beam Backprojection $$f(\vec{r}) = \quad (5)$$
$$\frac{1}{2\pi}\int_{\beta_0-\beta_r/2}^{\beta_0+\beta_r/2}\frac{R\|\vec{s}'(\beta)\|}{[(\vec{r}-\vec{s}(\beta))\cdot\vec{\phi}_{\beta,0,0}]^2}\int_{-\infty}^{\infty}[h(\gamma-\gamma')\cdot\tilde{g}(\beta,\gamma',\alpha)]d\gamma'd\beta,$$

$$\beta_r = \frac{2\pi}{H/D}\times\left(1-\frac{r_0}{R}\right), \quad (6)$$

where the function $h(\cdot)$ denotes the kernel of the filter (e.g., ramp, Shepp-Logan, or the like), $r_0$ represents the radius of the cylindrical support of the object, and D represents the detector height at the iso-center.

Once the backprojection view range is defined, the projection view data for the range is weighted (using techniques such as those described in Dennis L. Parker, "Optimal Short Scan Convolution Reconstruction for Fanbeam CT," *Med. Phys.* 9(2), March/April 1982, the contents of which are herein incorporated by reference), and convolved (using techniques analogous to those described in H. H. Barrett and W. Swindell, *Radiological Imaging: Theory of Image Formation, Detection, and Processing*, Vol. 2, New York: Academic Press, pp 391–392 (1981), the contents of which is herein incorporated by reference) as desired prior to backprojection.

Weighting functions used for helical scanning vary depending on helical pitch. Generally, over-scan functions are used for small helical pitch (projection range $\beta_r > 2\pi$) and extended half-scan for high helical pitch ($\beta_r \le 2\pi$) (See, e.g., M. D. Silver, K. Taguchi, and K. S. Han, "Field-of-view dependent helical pitch in multi-slice CT," Proc. of SPIE Med. Imag. Conf., 4320, 839–850 (2001); M. D. Silver, K. Taguchi, and I. A. Hein, "A simple algorithm for increased helical pitch in cone-beam CT," The Sixth International Meeting on Fully Three-Dimensional Image Reconstruction in Radiology and Nuclear Medicine, 70–73 (2001); C. R. Crawford and K. F. King, "Computed tomography scanning with simultaneous patient translation," Med. Phys. 17, 967–982 (1990); M. D. Silver, "A method for including redundant data in computed tomography," Med. Phys. 27, 773–774 (2000); and D. L. Parker, "Optimal short scan convolution reconstruction for fanbeam CT," Med. Phys. 9, 254–257 (1982), and the contents of each are hereby incorporated by reference.)

In the over-scan functions, weight is a function of projection angle, β, as shown in Equations 7–10 below:

$$os_{w_\beta} = (3x_\beta^2 - 2x_\beta^3)/2, \quad (7)$$

$$x_\beta = \begin{cases} \dfrac{\beta'}{\lambda_{OS}} & (0 \le \beta' < \lambda_{OS}) \\ 1 & (\lambda_{OS} \le \beta' < 2\pi) \\ \dfrac{2\pi + \lambda_{OS} - \beta'}{\lambda_{OS}} & (2\pi \le \beta' \le 2\pi + \lambda_{OS}) \\ 0 & (\text{otherwise}), \end{cases} \quad (8)$$

$$\beta' = \beta - (\beta_0 - \beta_r/2) = \beta - (\beta_0 - (2\pi + \lambda_{OS})/2), \quad (9)$$

$$\lambda_{OS} = \beta_r - 2\pi. \quad (10)$$

In the extended half-scan functions, weights are a function of ray angle, γ, as well as projection angle, β, as shown in Equations 11–14 below:

$$^{HS}w_{\beta,\gamma} = 3x_{\beta,\gamma}^2 - 2x_{\beta,\gamma}^3, \quad (11)$$

$$x_{\beta,\gamma} = \begin{cases} \dfrac{\beta'}{2(\Gamma-\gamma)} & (0 \le \beta' < 2(\Gamma-\gamma)) \\ 1 & (2(\Gamma-\gamma) \le \beta' < \pi + 2\gamma), \\ \dfrac{\pi + 2\Gamma - \beta'}{2(\Gamma+\gamma)} & (\pi - 2\gamma \le \beta' \le \pi + 2\Gamma) \\ 0 & (\text{otherwise}) \end{cases} \quad (12)$$

$$\beta' = \beta - (\beta_0 - \beta_r/2) = \beta - (\beta_0 - (\pi + 2\Gamma)/2), \quad (13)$$

$$2\Gamma = \beta_r - \pi. \quad (14)$$

One known weighting algorithm uses pixel dependent weighting during cone-beam backprojection, as well as pixel dependent projection angular range, which is often too complicated to implement. (See, e.g., Hu et al., U.S. Pat. No. 5,430,783, the contents of which are herein incorporated by reference.)

Another known weighting algorithm modifies extended half-scan by applying weight as a function of "pure cone-angle" to the projection data, modifying the projection data, and normalizing the weights of primary and complementary rays. (See, e.g., S. K. Patch, A. Nishide, A. Hagiwara, "Volumetric computed tomography data weights—Resolution vs artifact," *Radiology* 225(P), 496 (2002), the contents of which are herein incorporated by reference.)

$$x(\alpha, \beta, \gamma) = \frac{P(\beta,\gamma)^P \cdot (\cot\alpha)^{2a}}{P(\beta,\gamma)^P \cdot (\cot\alpha)^{2a} + P(\beta_c,\gamma_c)^P \cdot (\cot\alpha_c)^{2a}}, \quad (15)$$

where α is a parameter for tuning the algorithm and P is the normalized helical pitch.

Rewriting Equation 15 to obtain uniform notation, Equation 15 becomes:

$$^{ConeMHS}w_{\beta,\gamma,\alpha} = \frac{(^{MHS}w_{\beta,\gamma,\alpha})^{H/D} \cdot (\cot\alpha)^{2a}}{(^{MHS}w_{\beta,\gamma,\alpha})^{H/D} \cdot (\cot\alpha)^{2a} + (^{MHS}w_{\beta,\gamma,\alpha})^{H/D} \cdot (\cot\alpha_c)^{2a}}. \quad (16)$$

However, in the formula of Equations 15 and 16, altering the cone angle (cotα) or altering the original weight as a function of normalized helical pitch does not sufficiently reduce the effect of extrapolation or replication when the cone angle α is small. Additionally, the method of Equations 15 and 16 does not consider the validity (or potential invalidity) of the data being used. It is also important to note that the parameter "a" used in Equation 16 is distinct from the a of FIG. 8b.

FIG. 1a shows an example of the current weight at γ=0. One problem of the current method is that extending the projection angular range (as shown in FIGS. 1a and 1b) requires the use of extrapolated (or replicated) invalid data having the same weight as the valid (measured) data (FIG. 1b). Using such invalid data degrades image quality by introducing artifacts (and increasing noise if extrapolation is used).

Therefore, in light of the above-described difficulties, the present invention relates to applying another weight as a function of the validity of projection data and combining the other weight with overscan or extended half-scan, depending on helical pitch. Therefore, it is possible to extend the projection angular range for reconstruction while minimizing side effects of extrapolation and replication (FIG. 1c). If $\beta_r > 4\pi$, another weighting function should be applied that normalizes the weights to the primary and complementary rays. One such weighting function is shown below in Equation (D1):

$$\text{rot} = \text{floor}\frac{N}{N_{360}}$$

$$\text{overlap} = N - N_{360} \times \text{rot}$$

If($i == 0$)

Error. Should be MHS instead of OS else if($i$ $w_0 = 1/\text{rot}$ $$\text{weight}(n) = \begin{cases} \dfrac{n}{\text{overlap}} & 0 \le n < \text{overlap} \\ 1 & \text{overlap} \le n < \text{overlap} + N_{360} \times \text{rot}, \\ \dfrac{N-n-1}{\text{overlap}} & \text{overlap} + N_{360} \times \text{rot} \le n \le N-1 \end{cases}$$

where $N_{360}$ is the number of views per rotation and N is the number of preferred views for one slice.

First, the projection range of Equation (6) is enlarged to be:

$$\beta_r = \frac{2\pi}{H/(tD)} \times \left(1 - \frac{r_0}{R}\right); t > 1. \quad (17)$$

Cone-angle Dependent Weight: $^{row}w$

The data validity weighting function is set forth in equations 18–20, below:

$$^{Cone}w = a + (1-a) \cdot (3x_\alpha^2 - 2x_\alpha^2), \quad (18)$$

$$x_\alpha = \begin{cases} 1 & (|\alpha| \le \alpha_0) \\ \dfrac{\alpha_m - \alpha}{\alpha_m - \alpha_0} & (\alpha_0 < |\alpha| \le \alpha_m), \\ 0 & (\alpha_m < |\alpha|) \end{cases} \quad (19)$$

and $$\alpha_m > \tan^{-1}\frac{D}{2R}. \quad (20)$$

Figure 2:
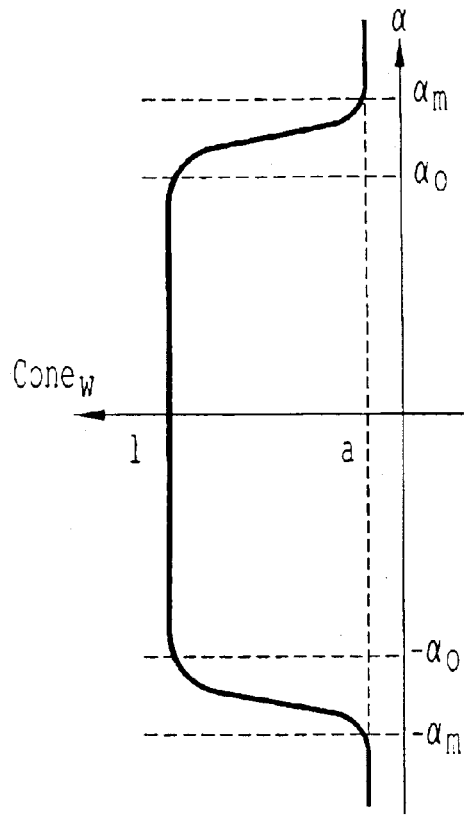
FIG. 2 illustrates Cone angle (or "validity of data") dependent weight, $^{Cone}w$.

Here, two cone-angles ($\alpha_0$ and $\alpha_m$) define the turning points of the validity curve (as shown in FIG. 2).

Figure 3A:
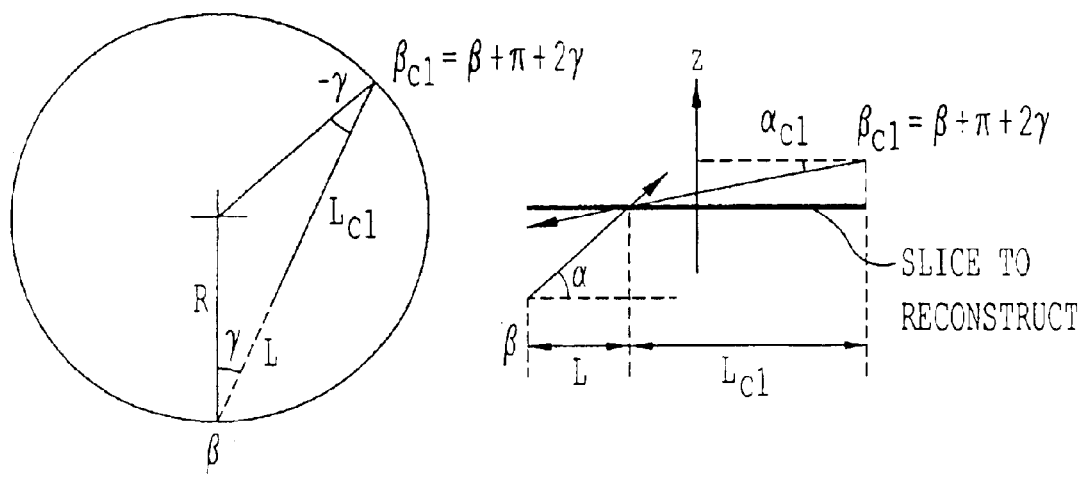
FIGS. 3a and 3b illustrate primary and complementary rays.
Figure 3B:
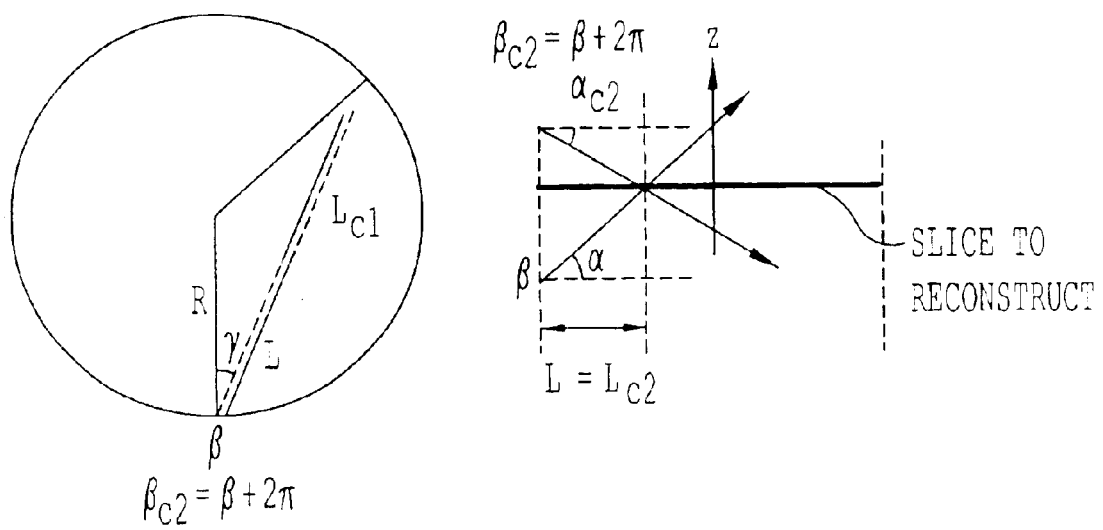

Complementary Ray: $d^C(\beta, \gamma, \alpha) = d^P(\beta_c, \gamma_c, \alpha_c)$ For each "primary ray $(d^P(\beta, \gamma, \alpha))$," it is possible to find corresponding "complementary rays $(d^{C(n)}(\beta, \gamma, \alpha))$" whose projected path onto the xy plane coincides with that of the primary ray. Specifically, the primary and complementary rays intersect the same point in the slice of interest (as illustrated in FIGS. 3a and 3b). The number of complementary rays may vary from 1 to 4, depending on $\beta_r$.

Functions for Complementary Rays

Projection angle and ray angle $$\beta_c = \begin{cases} \beta + \pi + 2\gamma & (\beta + \pi + 2\gamma \leq \pi) \\ \beta - \pi + 2\gamma & (\text{otherwise}) \end{cases} \quad (B1)$$

$$\gamma_c = -\gamma \quad (B2)$$

Cone angle

The z coordinates of each focus and the cone angle to the voxel of interest are defined by:

$$z = -\frac{\beta}{2\pi} \cdot l; \; z_c = -\frac{\beta_c}{2\pi} \cdot l, \; \text{and} \quad (B3)$$

$$\alpha = \tan^{-l}\frac{z}{L}; \; \alpha_c = \tan^{-l}\frac{z_c}{L_c}. \quad (B4)$$

Thus, $$L = \frac{z}{\tan\alpha}; \; L_c = \frac{z_c}{\tan\alpha_c}. \quad (B5)$$

From Figs. 3a and 3b:

$$L + L_c = 2R\cos\gamma. \quad (B6)$$

Using the above equations:

$$\alpha_c = \tan^{-l}\frac{\frac{-\beta_c}{2\pi} \cdot l}{2R\cos\gamma - L} \quad (B7)$$

$$= \begin{cases} \tan^{-l}\left[\frac{-l \cdot \tan\alpha \cdot (\beta + \pi + 2\gamma)}{4\pi R \cdot \tan\alpha \cdot \cos\gamma + \beta \cdot l}\right] & (\beta + \pi + 2\gamma \leq \pi) \\ \tan^{-l}\left[\frac{-l \cdot \tan\alpha \cdot (\beta - \pi + 2\gamma)}{4\pi R \cdot \tan\alpha \cdot \cos\gamma + \beta \cdot l}\right] & (\text{otherwise}) \end{cases}$$

Figure 4A:
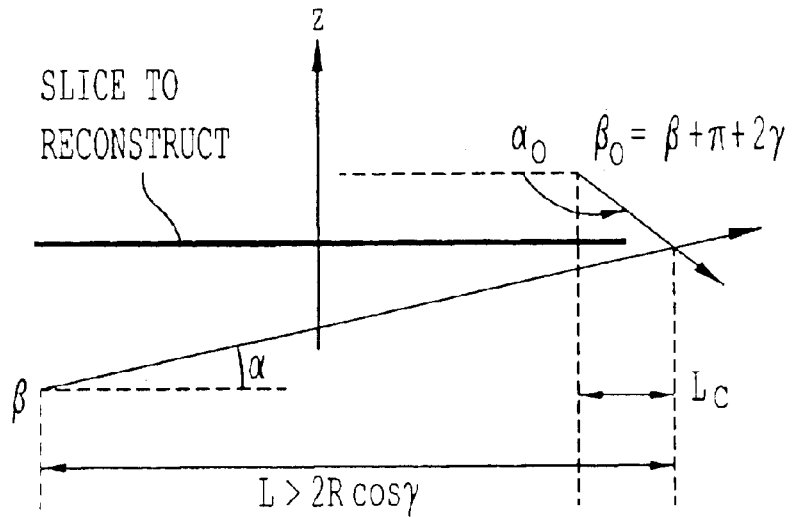
FIG. 4 illustrates cases when the $\alpha_c$ calculated becomes strange value.
Figure 4B:
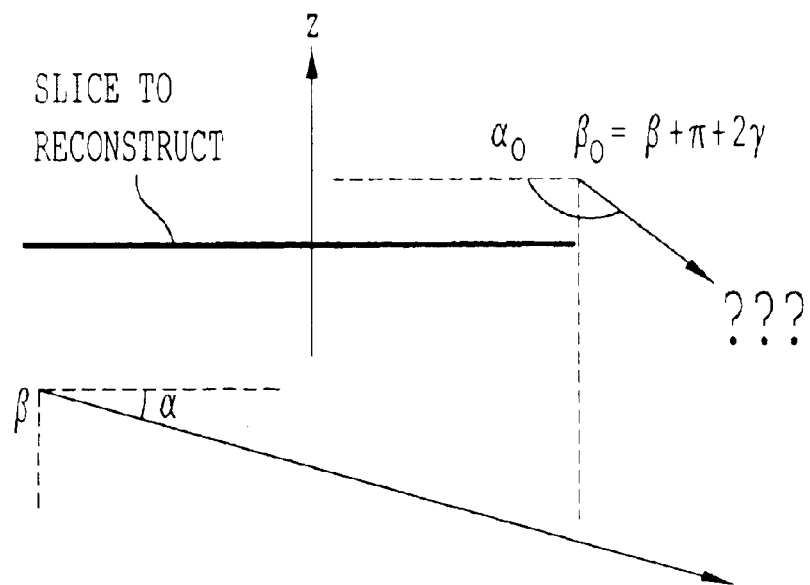
Figure 5:
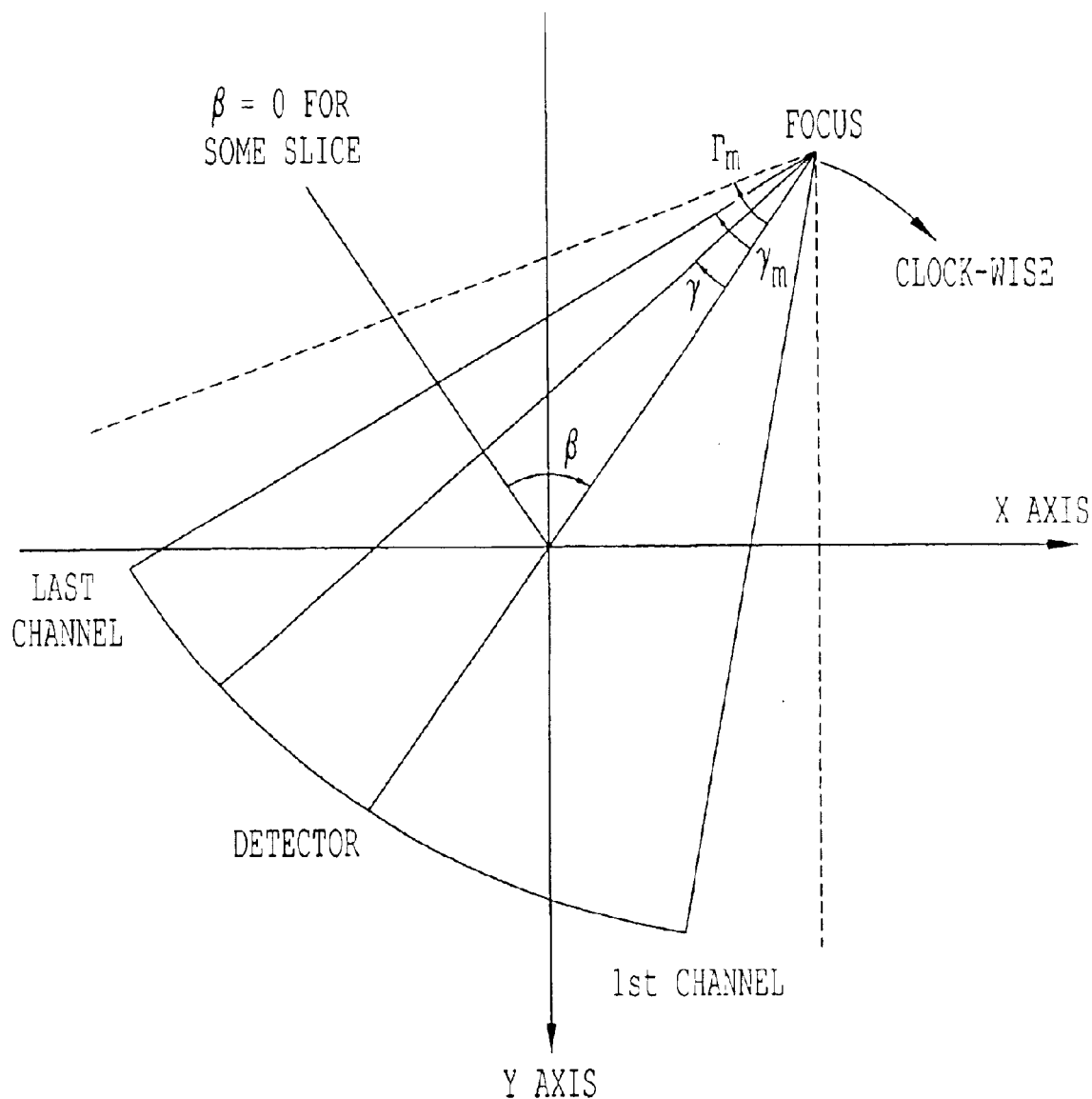
FIG. 5 illustrates geometry of backprojection, specifically a projection angle, $\beta$, a ray-angle, $\gamma$, and a virtual fan-angle, $\Gamma_m$.

It is useful to restrict $\alpha_c$ as shown in Equation (B8) to avoid extraordinary cases, such as those shown in FIG. 4.

$$\alpha_c = \begin{cases} \alpha_0 + \alpha_m & (|\alpha_c| > \alpha_0 + \alpha_m) \\ \alpha_c & (\text{otherwise}) \end{cases} \quad (B8)$$

When the ray-sum of $\alpha$ does not pass through the slice of interest inside of the scan orbit, calculating $\alpha_c$ is meaningless and $\alpha_c$ can have a strange value. In this case, the MHS weight $w_o$ must be zero for such ray and $\alpha_c$ does not affect results at all. When $\beta=0$ and $\alpha=0$, $\alpha_c$ is unknown: one complementary ray cannot be identified. However, it is not necessary to consider this case because in the current detector configuration, $\alpha$ cannot be 0. (The center of any detector row is not located at the mid-plane.) If the detector configuration is changed and there is a case for $\alpha=0$, MHS may still be performed because the MHS weight for $\beta=0$ and $\beta=2\pi$ is 0.

Figure 10A:
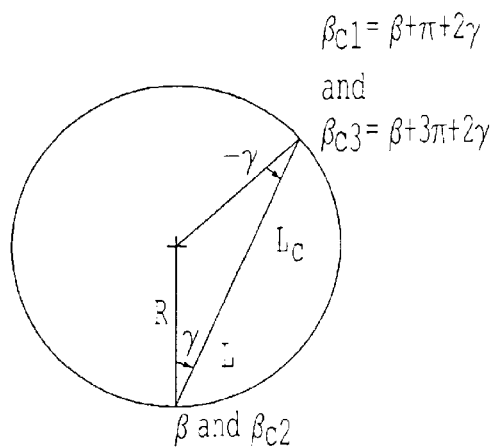
FIGS. 10a, 10b, 10c, 10d, and 10e show direct and complementary rays.
Figure 10B:
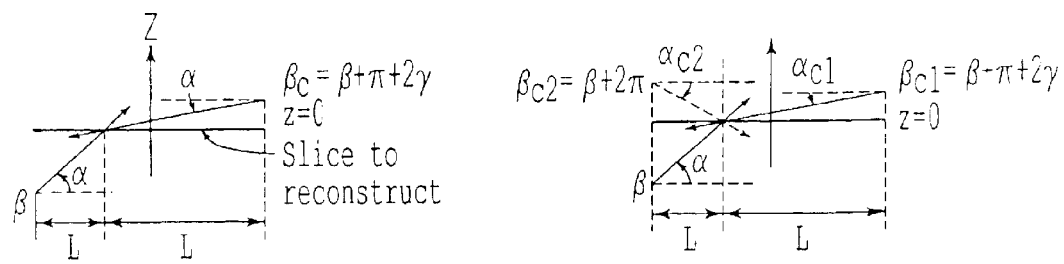
Figure 10B:
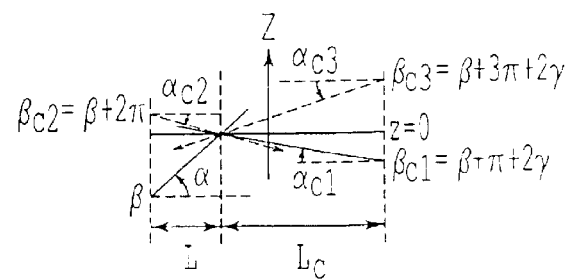
Figure 10C:
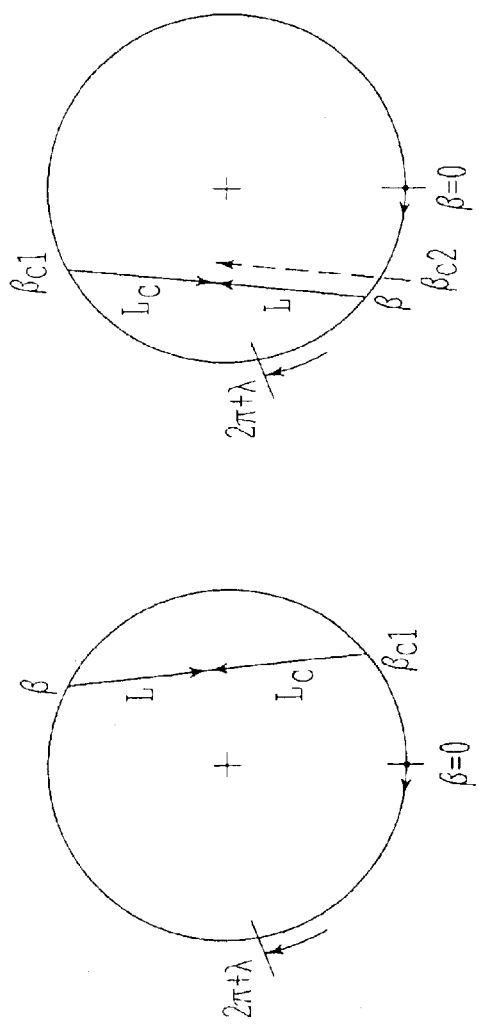
Figure 10D:
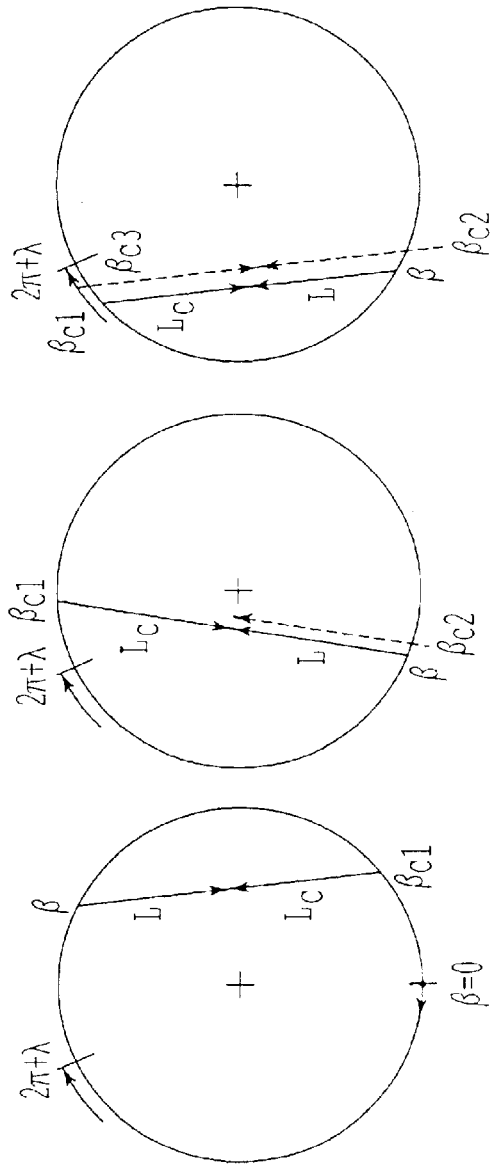
Figure 10E:
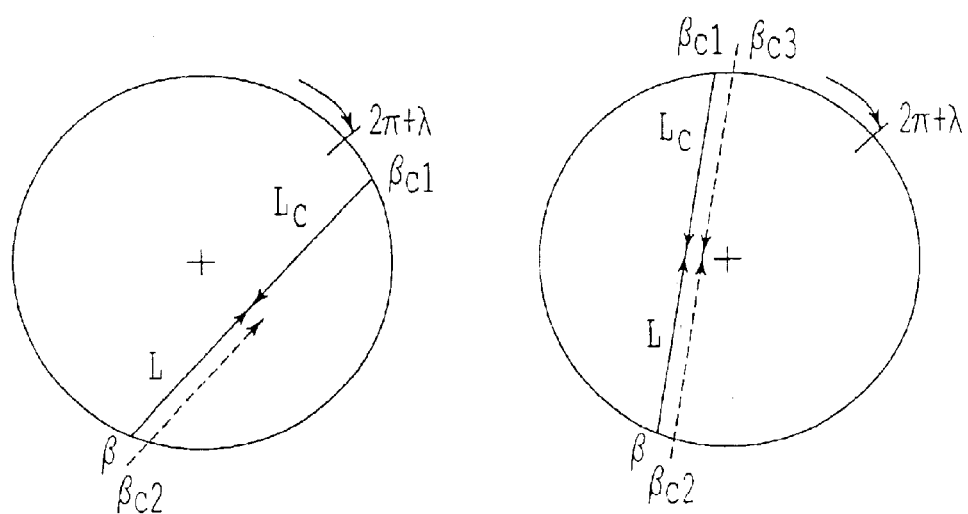
Figure 11A:
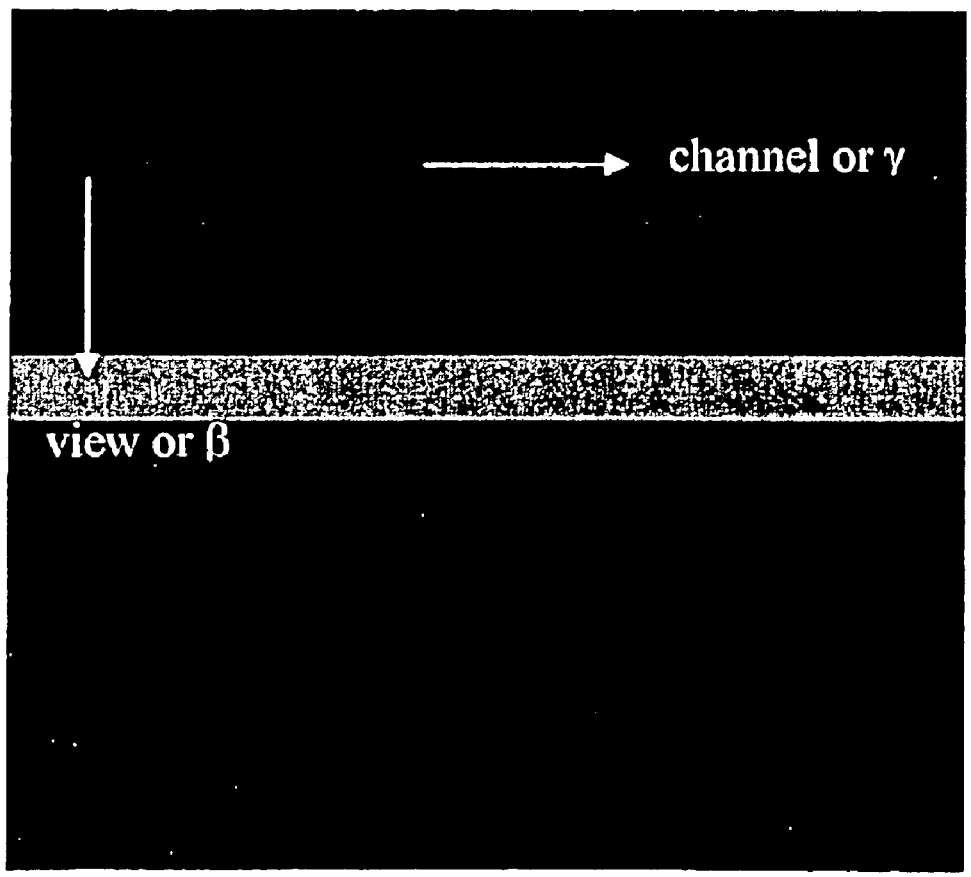
FIGS. 11a–11e illustrate results using the OS method.
Figure 11B:
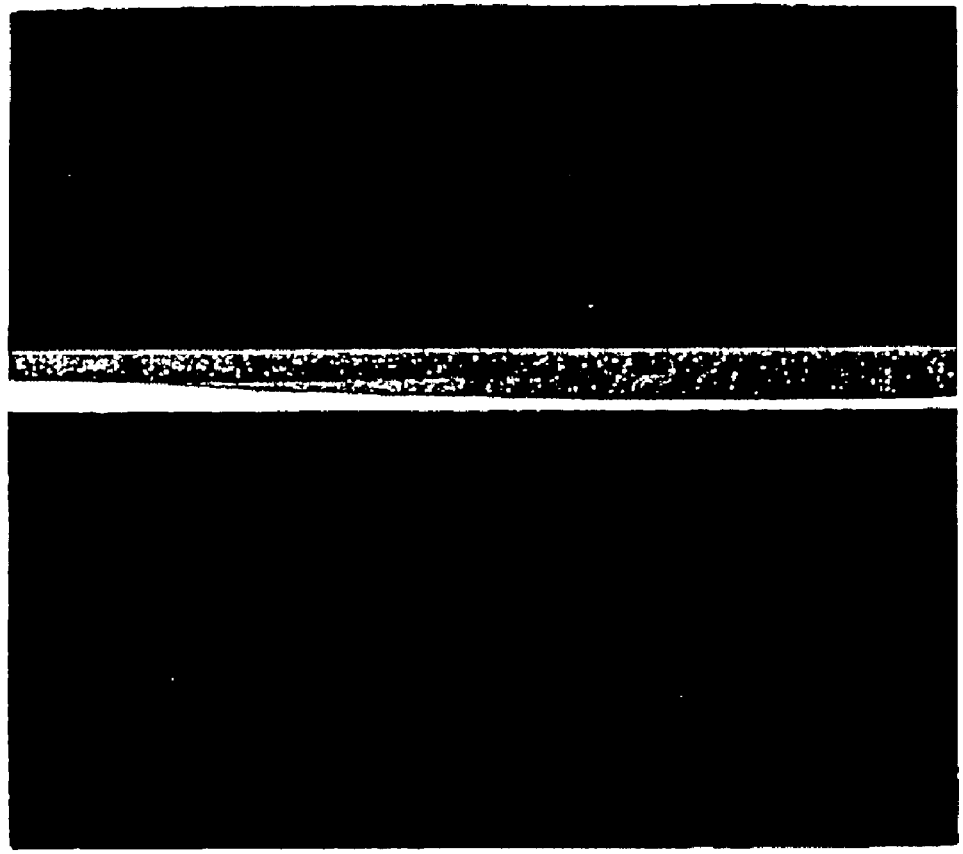
Figure 11C:
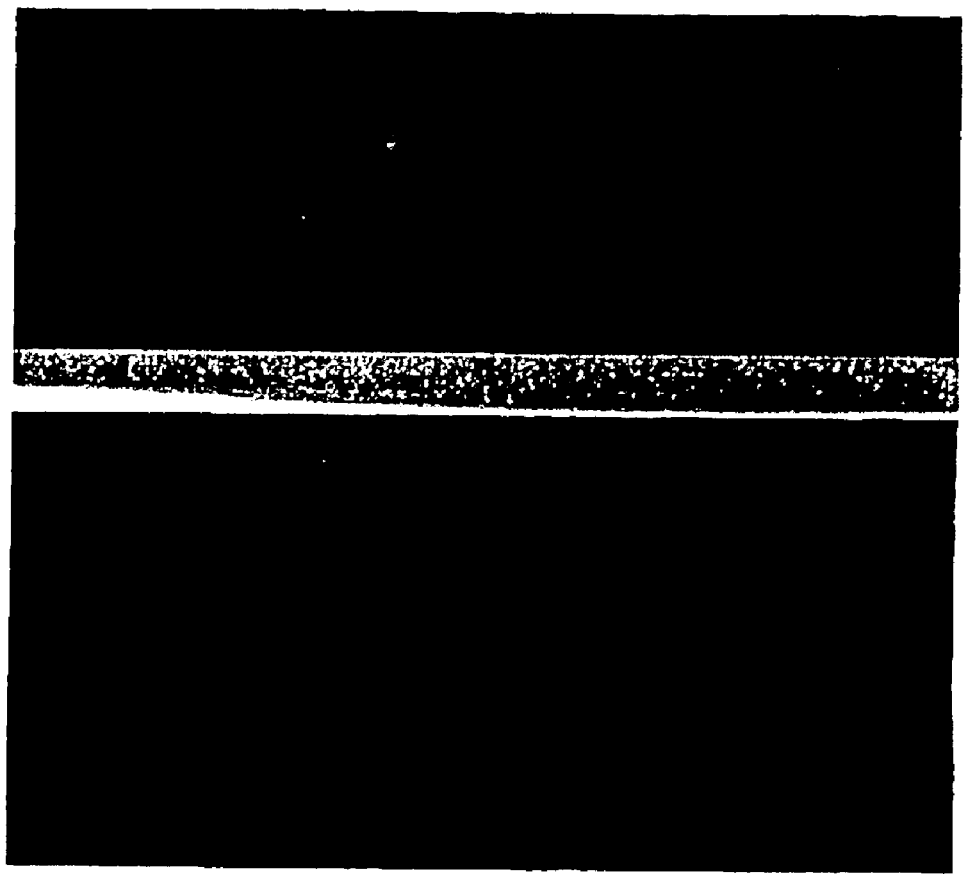
Figure 11D:
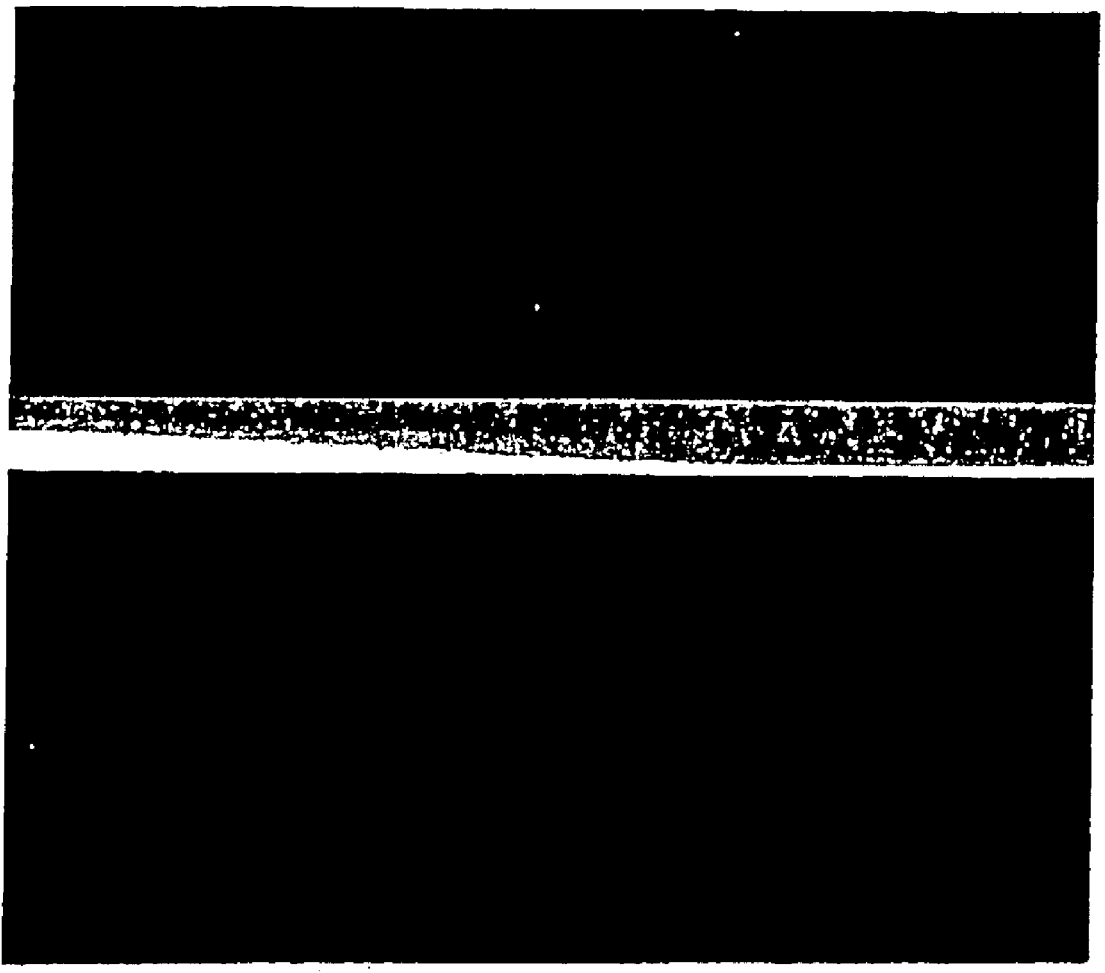
Figure 11E:
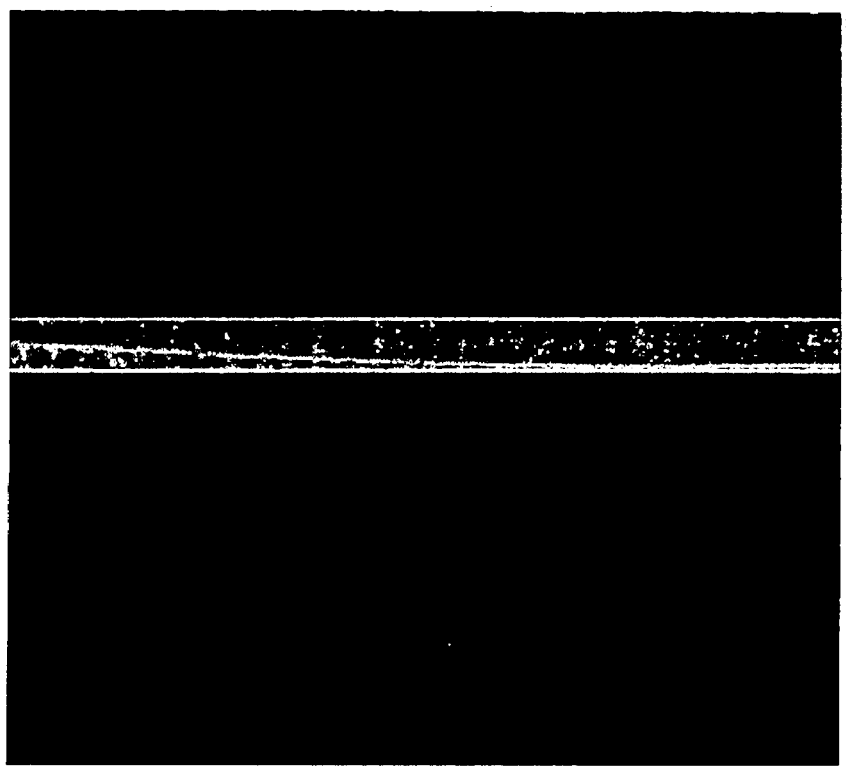
Figure 12A:
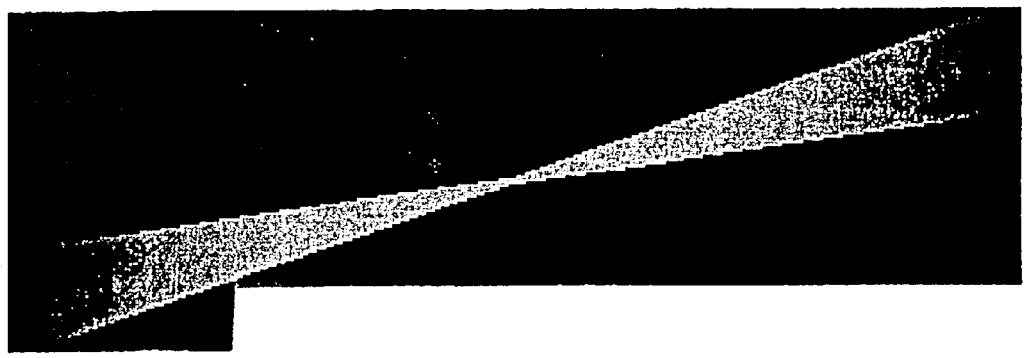
FIGS. 12a–12e and 13a–13e illustrate results using the current OS method.
Figure 12B:
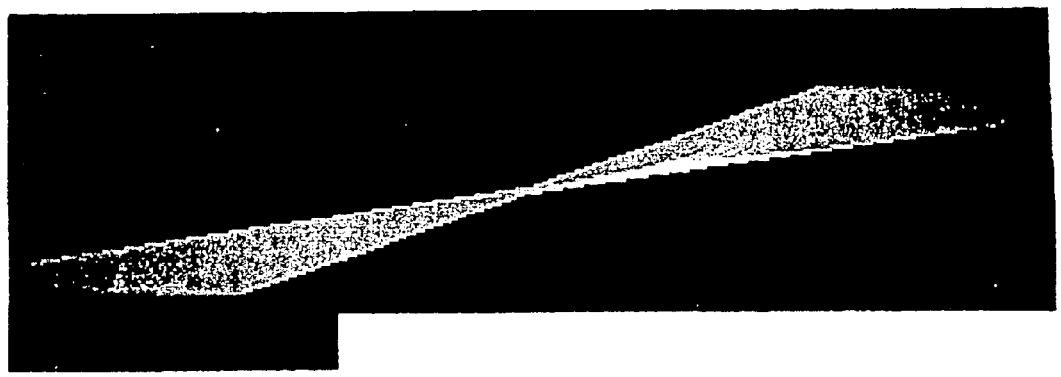
Figure 12C:
Figure 12D:
Figure 12E:
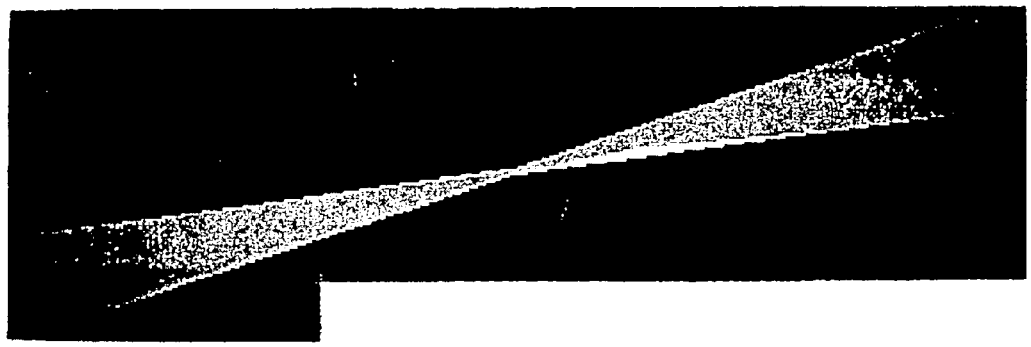
Figure 13A:
Figure 13B:
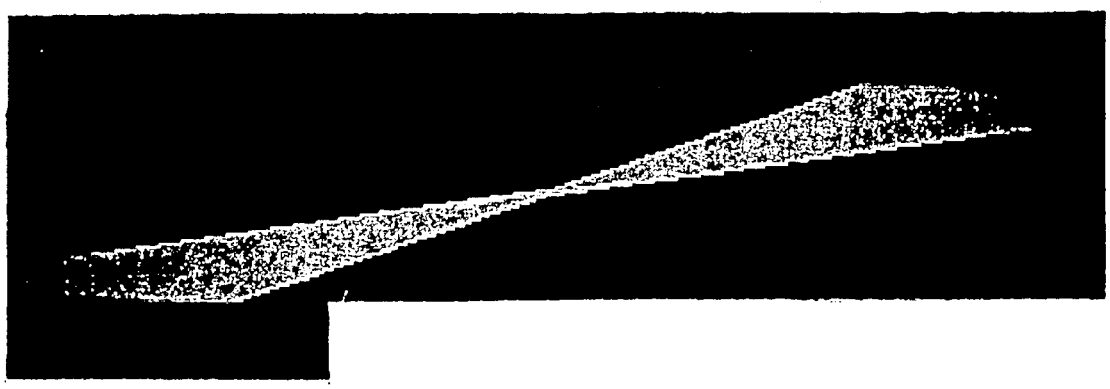
Figure 13C:
Figure 13D:
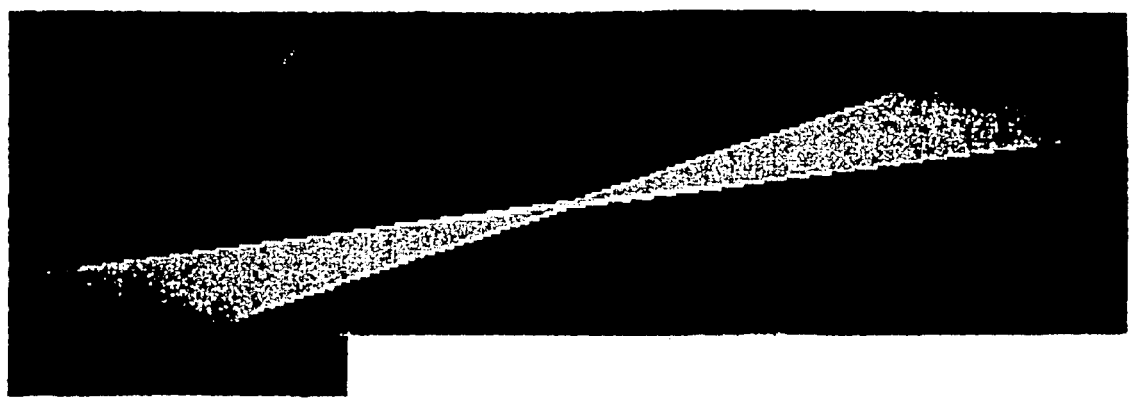
Figure 13E:

The complementary rays may be obtained when positions of focus and detector are exchanged (as shown in FIG. 10a) or at the same projection angle but in the different rotation (as shown in FIG. 10b). Let $$\beta_h = (2\pi + \lambda)/2. \quad (C1)$$

There are two ways to obtain complementary rays: (1) using 6 complementary rays (the previous 3 rays and the following 3 rays) all the time without boundary conditions (the OS weight dismisses the non-existing rays automatically); or (2) using the "valid" complementary rays by considering the boundary conditions. The advantages of the former method include (1a) no need to bother with boundary conditions, and thus, (1b) simple coding. The advantages of the later method include (2a) a shorter processing time because all of the calculated rays are used (no waste rays).

The Method Using Six Complementary Rays All the Time

Projection angle and ray angle $$\begin{cases} \beta_{c1} = \beta + \pi + 2\gamma \\ \gamma_{c1} = -\gamma \end{cases}, \quad (C2)$$

$$\begin{cases} \beta_{c2} = \beta + 2\pi \\ \gamma_{c2} = \gamma \end{cases}, \quad (C3)$$

$$\begin{cases} \beta_{c3} = \beta + 3\pi + 2\gamma = \beta_{c1} + 2\pi \\ \gamma_{c3} = -\gamma = \gamma_{c1} \end{cases}, \quad (C4)$$

$$\begin{cases} \beta_{c(-1)} = \beta - \pi + 2\gamma = \beta_{c1} - 2\pi \\ \gamma_{c(-1)} = -\gamma = \gamma_{c1} \end{cases}, \quad (C5)$$

$$\begin{cases} \beta_{c(-2)} = \beta - 2\pi \\ \gamma_{c(-2)} = \gamma \end{cases}, \quad (C6)$$

$$\begin{cases} \beta_{c(-3)} = \beta - 3\pi + 2\gamma = \beta_{c(-1)} - 2\pi \\ \gamma_{c(-3)} = -\gamma = \gamma_{c(-1)} \end{cases}. \quad (C7)$$

When $\beta=\beta_h$ and $\alpha=0$, $\alpha_c$ is unknown: one complementary ray cannot be identified. However, it is not necessary to consider this case because in the current detector configuration, $\alpha$ cannot be 0. (The center of any detector row is not located at the mid-plane.) If the detector configuration is changed and there is a case for $\alpha=0$, the configuration will be still okay for MHS because the MHS weight for $\beta=0$ and $\beta=2\pi$ is 0. Additionally, in the OS case, it is possible to calculate two $\alpha_c$, one for $\beta=\beta_h-d\beta$ and the other for $\beta=\beta_h+d\beta$, and average them.

The complementary ray can be defined by using the following Equations 21 and 22.

The projection angle and the ray angle of n-complementary ray is defined by:

$$\beta_{c(n)} = \begin{cases} \beta + n\pi + 2\gamma & (n = \text{odd}) \\ \beta + 2n\pi & (n = \text{even}) \end{cases}, \quad (21)$$

$$\gamma_{c(n)} = \begin{cases} -\gamma & (n = \text{odd}) \\ \gamma & (n = \text{even}) \end{cases}. \quad (22)$$

The projected "in-plane" distances from the focus to the voxel of interest for primary and complementary ray are:

$$L = z_p/\tan\alpha, \quad (23)$$

In order to avoid strange cases like $L > R + r_0$ (FIG. 101), L is clipped by:

$$L = \begin{cases} R + r_0/2 & (L > R + r_0/2) \\ R - r_0/2 & (L < R - r_0/2) \\ L & (\text{otherwise}) \end{cases}. \quad (23a)$$

Subsequently, $$L_{c(n)} = \begin{cases} 2R\cos\gamma - L & (n = \text{odd}) \\ L & (n = \text{even}) \end{cases}, \quad (24)$$

$$z_\beta = -(\beta - \beta_0) \cdot H / 2\pi, \quad (25)$$

where $z_\beta$ denotes the z distance from each focus to the plane to reconstruct.

The cone-angle for the complementary ray is:

$$\alpha_c = \tan^{-1}(z_{\beta(n)} / L_{c(n)}) \quad (26)$$

$$= \begin{cases} \tan^{-1}\dfrac{-(\beta + n\pi + 2\gamma - \beta_0)H}{2\pi(2R\cos\gamma - L)} & (n = \text{odd}) \\ \tan^{-1}\dfrac{(\beta + 2n\pi - \beta_0)H}{2\pi L} & (n = \text{even}) \end{cases}.$$

Figure 8A:
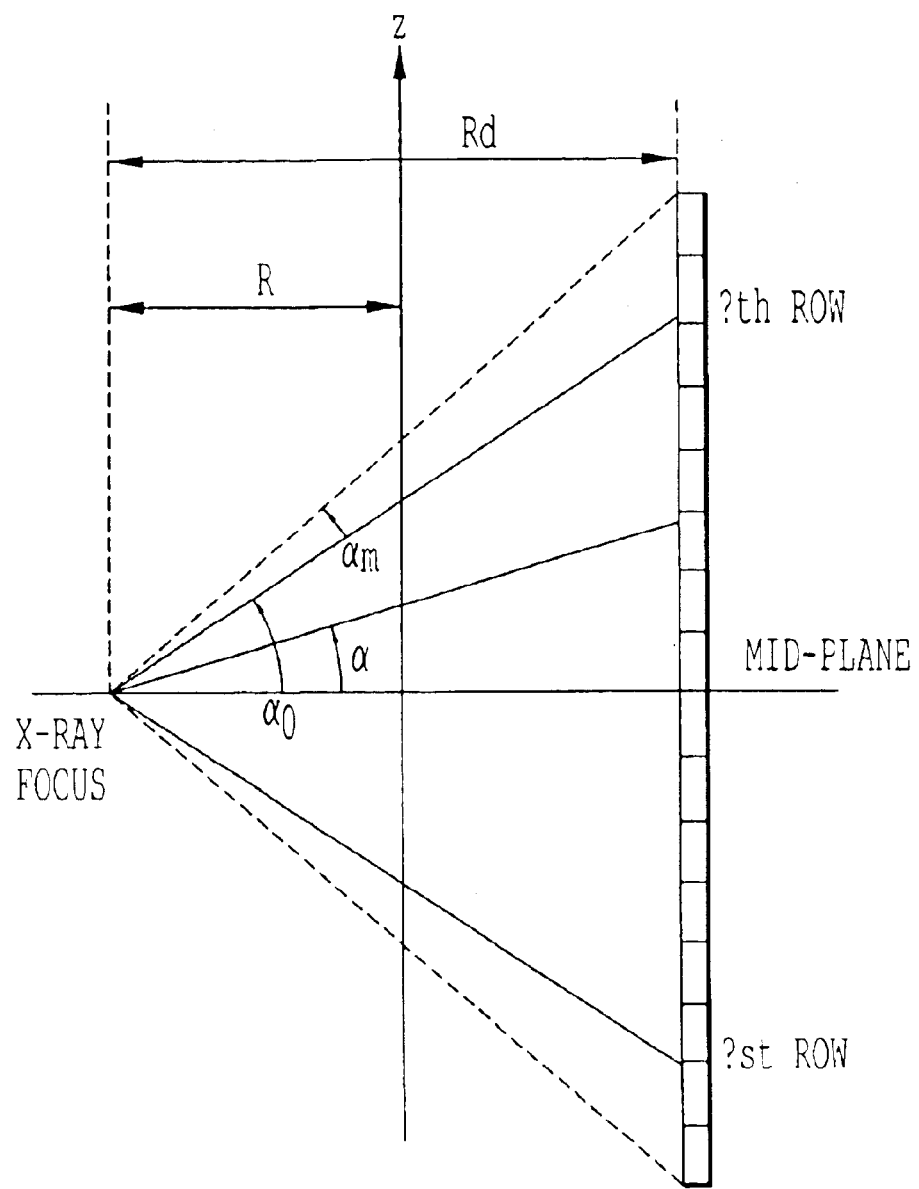
FIG. 8a illustrates the parameters related to the cone angle, $\alpha$, $\alpha_0$, and $\alpha_m$.
Figure 8B:
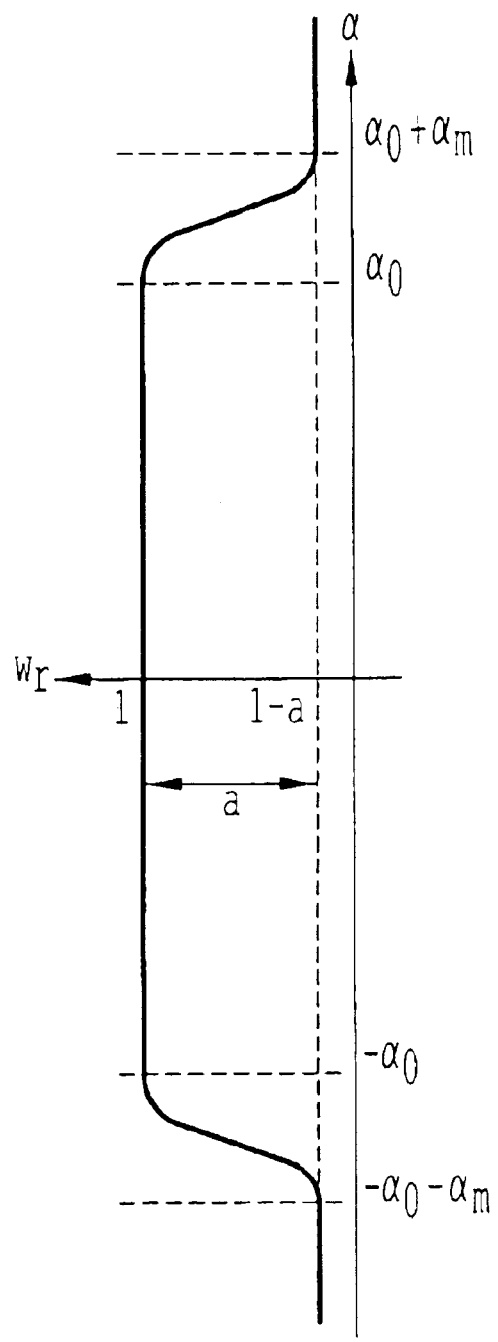
FIG. 8b depicts weighting as a function of cone angle.
Figure 9:
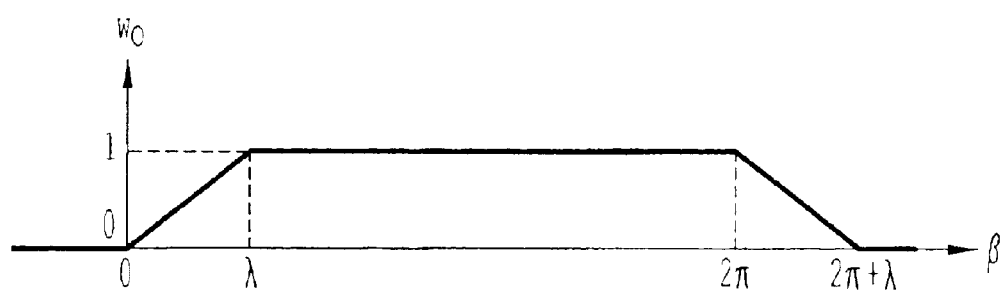
FIG. 9 represents a weighting function of OS.

Again, restrict the angle for avoiding unnecessary cases. Specifically, Equation (26a) is used to calculate the cone-angle value. However, because the weighting curve shown in FIG. 8b is flat in regions where ($\alpha > \alpha_m$), clipping the cone-angle at $\alpha_m$ yields the same result.

$$\alpha_c = \begin{cases} \alpha_m & (|\alpha_c| > \alpha_m) \\ \alpha_c & (\text{otherwise}) \end{cases}. \quad (26a)$$

Note that when n=0, Equations 21–26 give a primary ray.

Finally, the weights of overscan and half-scan are modified as shown in Equations 27 and 28 and used in Equation 3.

$$^{ConeOS}w_{\beta,\gamma,\alpha} = \frac{^{OS}w_\beta \cdot {}^{Cone}w_{\beta,\gamma,\alpha}}{\sum_{n=-3}^{3}\left(^{OS}w_{\beta_{c(n)}} \cdot {}^{Cone}w_{\beta_{c(n)},\gamma_{c(n)},\alpha_{c(n)}}\right)}, \quad (27)$$

and $$^{ConeHS}w_{\beta,\gamma,\alpha} = \frac{^{HS}w_{\beta,\gamma} \cdot {}^{Cone}w_{\beta,\gamma,\alpha}}{\sum_{n=-1}^{1}\left(^{HS}w_{\beta_{c(n)},\gamma_{c(n)}} \cdot {}^{Cone}w_{\beta_{c(n)},\gamma_{c(n)},\alpha_{c(n)}}\right)}. \quad (28)$$

The method described above has several advantages. First, the method of the present embodiment decreases weights to the invalid (extrapolated/replicated) rays and increases weight to the valid (measured) rays. Additionally, weights are normalized so that the redundancy of data is correctly compensated. Moreover, the method of the present embodiment will not change weights if all ray-sums are valid, all ray-sums are invalid, or there is no redundant data. Finally, the weight is a function of $\beta$, $\gamma$, and $\alpha$ in all helical pitches, and smoothly changes in any direction.

The cone angle dependent weight as described by $^{Cone}w$ (Equations (18–20)), may be arbitrary. It may include a sigmoid curve, an exponential, or the like. The weighting function, which is combined with $^{Cone}w$, may also be arbitrary. Even if cone angle dependent weight has been used, the method of the first embodiment is capable of enhancing performance by taking validity of each ray-sum into account. The reconstruction method of the present invention does not have to be "cone-beam," and may include such methods as parallel-fan-beam by rebinning (sorting) cone-beam data obtained at plural focus (cone vertexes) (like fan-to-parallel beam rebinning) and the like.

Additionally, according to a second aspect of the present invention, it is possible to modify the first embodiment to avoid giving too large a weight to the valid ray-sums.

When $wt_{max}$, has, for example, a value of 0.6, then $$sw_{\beta,\gamma} = \sum_{n=-3}^{3} {}^{OS}w_{\beta_{c(n)}} \cdot {}^{Cone}w_{\beta_{c(n)},\gamma_{c(n)},\alpha_{c(n)}} \quad (29)$$

or $$sw_{\beta,\gamma} = \sum_{n=-1}^{1} {}^{MHS}w_{\beta_{c(n)}} \cdot {}^{Cone}w_{\beta_{c(n)},\gamma_{c(n)},\alpha_{c(n)}}, \quad (30)$$

and $$^{ConeOS}w_{\beta,\gamma,\alpha} = \begin{cases} wt_{max}, & (^{Cone}w_{\beta,\gamma,\alpha} \cdot {}^{OS}w_{\beta,\gamma,\alpha} = w_m \text{ and } sw_{\beta,\gamma}/w_m \leq 1/wt_{max}) \\ \dfrac{^{Cone}w_{\beta,\gamma,\alpha} \cdot {}^{OS}w_{\beta,\gamma,\alpha} \times (1 - wt_{max})}{^{Cone}w_{\beta,\gamma,\alpha} \cdot {}^{OS}w_{\beta,\gamma,\alpha} + sw_{\beta,\gamma} - 1/2}, & (^{Cone}w_{\beta,\gamma,\alpha} \cdot {}^{OS}w_{\beta,\gamma,\alpha} \neq w_m \text{ and } sw_{\beta,\gamma}/w_m \leq 1/wt_{max}) \\ \dfrac{^{Cone}w_{\beta,\gamma,\alpha} \cdot {}^{OS}w_{\beta,\gamma,\alpha}}{^{Cone}w_{\beta,\gamma,\alpha} \cdot {}^{OS}w_{\beta,\gamma,\alpha} + sw_{\beta,\gamma}}, & (\text{otherwise}) \end{cases} \quad (31)$$

or $$^{ConeMHS}w_{\beta,\gamma,\alpha} = \begin{cases} wt_{max}, & (^{Cone}w_{\beta,\gamma,\alpha} \cdot {}^{MHS}w_{\beta,\gamma,\alpha} = w_m \text{ and } w_m \geq sw_{\beta,\gamma} \cdot wt_{max}) \\ \dfrac{^{Cone}w_{\beta,\gamma,\alpha} \cdot {}^{MHS}w_{\beta,\gamma,\alpha} \times (1 - wt_{max})}{sw_{\beta,\gamma} - wt_{max}}, & (^{Cone}w_{\beta,\gamma,\alpha} \cdot {}^{MHS}w_{\beta,\gamma,\alpha} \neq w_m \text{ and } w_m \geq sw_{\beta,\gamma} \cdot wt_{max}) \\ \dfrac{^{Cone}w_{\beta,\gamma,\alpha} \cdot {}^{MHS}w_{\beta,\gamma,\alpha}}{sw_{\beta,\gamma}}, & (\text{otherwise}) \end{cases} \quad (32)$$

where $w_m$ is the maximum weight among all the primary and the complementary rays $$(^{OS}w_{\beta c(n)} \cdot {}^{Cone}w_{\beta c(n),\gamma c(n),\alpha c(n)} \text{ or } {}^{MHS}w_{\beta c(n)} \cdot {}^{Cone}w_{\beta c(n),\gamma c(n),\alpha c(n)}), \quad (33)$$

The method according to the above-described second aspect of the present invention provides decreased image noise. The noise is most effectively reduced when data are weighted equally. The first embodiment sometimes results in disproportionate weighting of the data, which causes increased image noise. By capping the value at $\alpha_m$, it is possible to achieve a better balancing of the validity of the data, the ability to reduce image noise, and the image quality.

Additionally, according to a third aspect of the present invention, it is possible to obtain a more efficient method of data weighting. The third embodiment method does not search non-existing ray-sums. For example, in a case of MHS weighting, the projection data ranges for $2\pi$. Therefore, it is possible to use Equation (34) instead of Equation (21), thereby reducing the number of complementary ray-sums to calculate from 3 to 2.

$$\beta_{c(n=1)} = \begin{cases} \beta + \pi + 2\gamma & (\beta' + 2\gamma \le \pi) \\ \beta - \pi + 2\gamma & \text{(otherwise)} \end{cases} \quad (34)$$

The Method Using Six Complementary Rays All the Time in OS $$wt_{\alpha,\beta,\gamma} = \frac{w_r(\alpha) \cdot w_{o,\beta}}{w_r(\alpha) \cdot w_{o,\beta} + \sum_{n=-3}^{-1} w_r(\alpha_{c(n)}) \cdot w_{oc(n),\beta c(n),\gamma(n)} + \sum_{n=1}^{3} w_r(\alpha_{cn}) \cdot w_{ocn,\beta cn,\gamma n}}, \quad (C1)$$

where $$x(\alpha) = \begin{cases} 0 & |\alpha| \le \alpha_0 \\ (|\alpha| - \alpha_0)/\alpha_m & \alpha_0 < |\alpha| \le \alpha_0 + \alpha_m \\ 1 & \alpha_0 + \alpha_m < |\alpha| \end{cases} \quad (C2)$$

and $$w_r = 1 - a \cdot (3x^2 - 2x^3). \quad (C3)$$

Note: $0 < a < 1$.

When $a = 0$, Eq. (C1) provides OS weight, $wt_{\alpha,\beta,\gamma} = w_{o,\beta}$.

Figure 14:
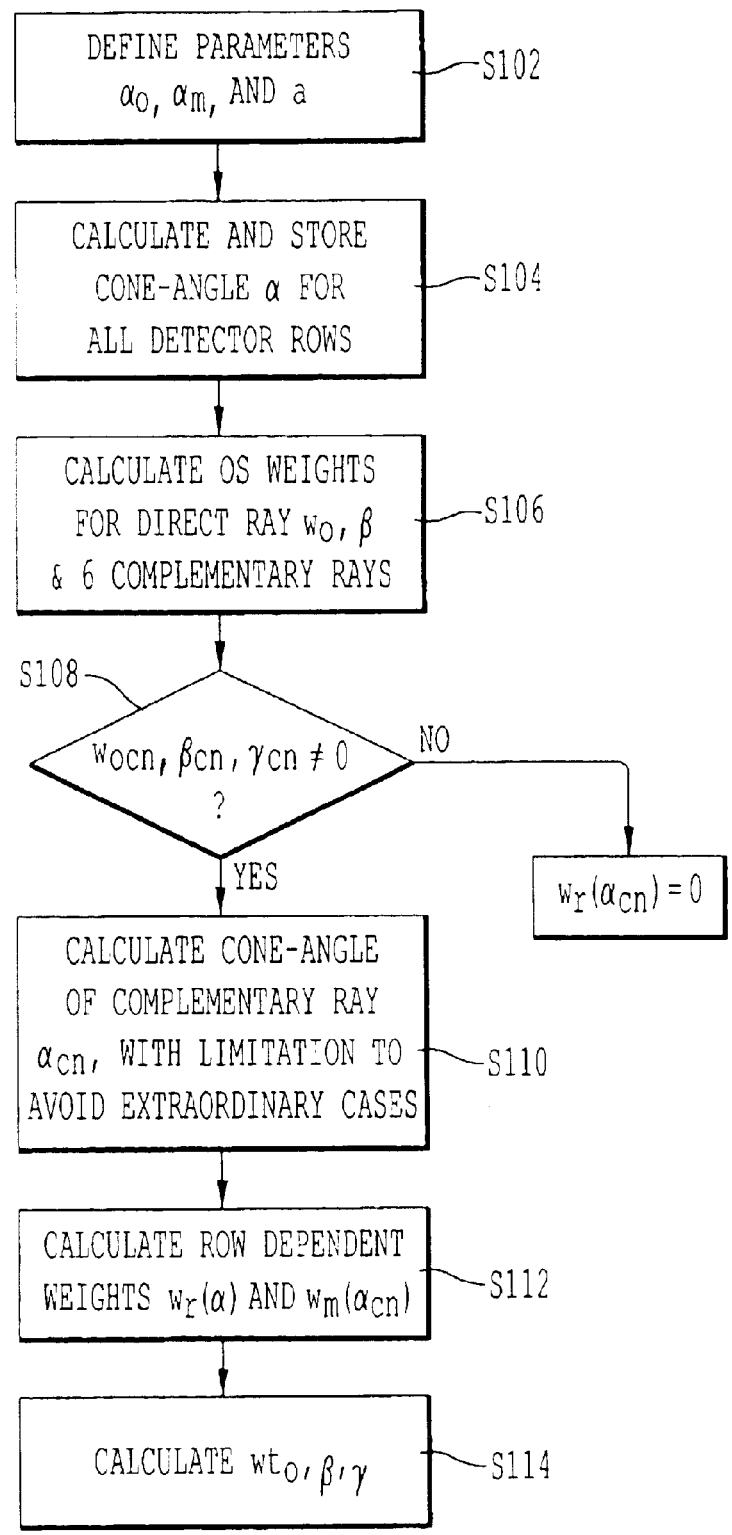
FIG. 14 depicts the method of using six complementary rays all the time.

As illustrated in FIG. 14, the method for using six complementary rays all the time includes several steps. The method begins with step S102: Define parameters $\alpha_0$, $\alpha_m$, and a. Step S104: Calculate and store cone-angle $\alpha$ for all of detector rows. Step S106: Calculate OS weights for direct ray $w_{o,\beta}$ and 6 complementary rays $w_{ocn,\beta cn,\gamma cn}$. Step S108: If $w_{ocn,\beta cn,\gamma cn} \ne 0$, do steps S110 and S112. Else if $w_{ocn,\beta cn,\gamma cn} = 0$, let $w_r(\alpha_{cn}) = 0$. Calculate cone-angle of complementary ray, $\alpha_{cn}$, with limitation for avoiding extraordinary cases. Step S112: Calculate row dependent weights $w_r(\alpha)$ and $w_m(\alpha_{cn})$. Step S114: Calculate $wt_{o,\beta,\gamma}$ by Equation (C1), shown above.

The Method to Use Valid Complementary Rays Only in OS

A similar approach can be taken for OS or other weighting methods to reduce the number of ray-sums from 7 to 4. First, the weight is applied. Then, the two weights for the direct ray and the complementary ray are normalized.

$$wt_{\alpha,\beta,\gamma} = \frac{w_r(\alpha) \cdot w_{o,\beta}}{w_r(\alpha) \cdot w_{o,\beta} + \sum_{n=1}^{3} w_r(\alpha_{cn}) \cdot w_{ocn,\beta cn,\gamma n}}. \quad (C1)'$$

Figure 15:
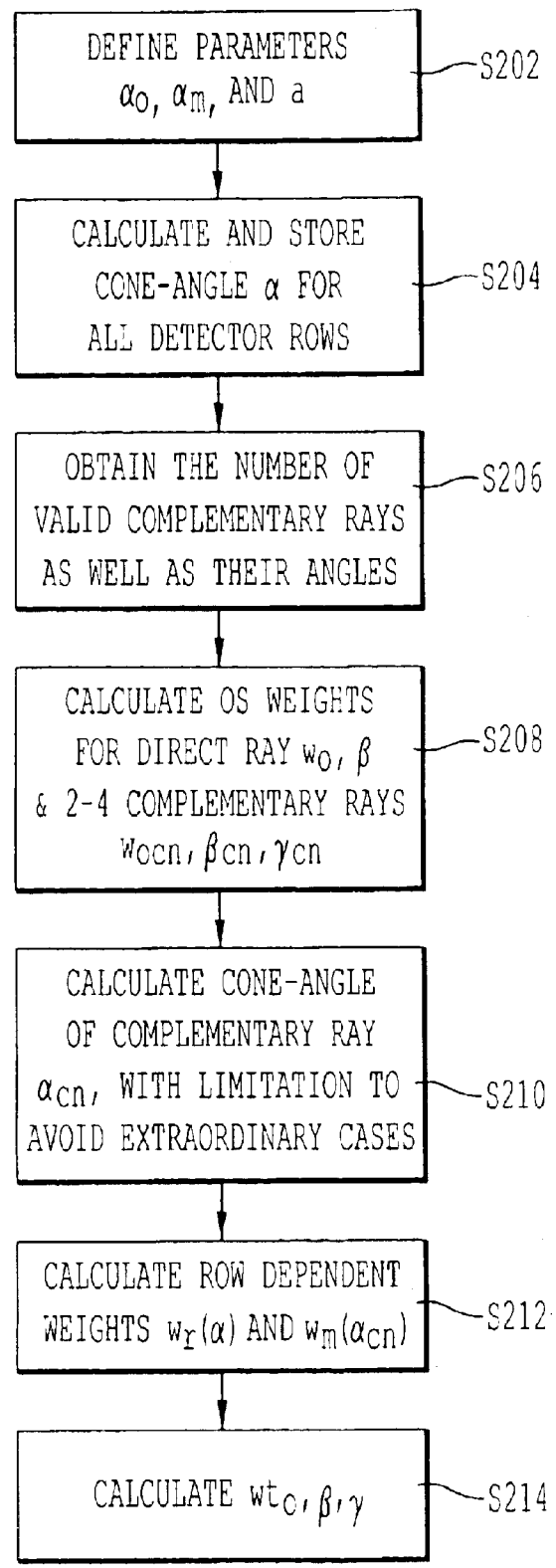
FIG. 15 depicts the method using only valid complementary rays.

The method for using valid complementary rays only is shown in FIG. 15. The method includes several steps, beginning with step S202: Define parameters $\alpha_0$, $\alpha_m$, and a. Step S204: Calculate and store cone-angle $\alpha$ for all of detector rows. Step S206: Obtain the number of valid complementary rays as well as their angles. Step S208: Calculate OS weights for direct ray $w_{o,\beta}$ and 2–4 complementary rays $w_{ocn,\beta cn,\gamma cn}$. Step S210: Calculate cone-angle of complementary ray, $\alpha_{cn}$, with limitation for avoiding extraordinary cases. Step S212: Calculate row dependent weights $w_r(\alpha)$ and $w_m(\alpha_{cn})$. Step S214: Calculate $wt_{o,\beta,\gamma}$ by Equation (C1)'.

An example of parameters is shown below:

$$\alpha_0 = \tan^{-1}\frac{d \cdot \left(\frac{Nrow-1}{2} + r1\right)}{R}, \quad (D1)$$

$$\alpha_m = \tan^{-1}\frac{d \cdot \left(\frac{Nrow-1}{2} + r2\right)}{R} - \alpha_0, \quad (D2)$$

$$a = 0.9. \quad (D3)$$

Examples of row-OS weight are shown in FIGS. 11–13. Note that these figures only show detector rows used in reconstruction. FIG. 11b: When (r2−r1) is small, we observe rapid change in view direction as well as whip-type pattern. When (r2−r1) is large, this change and whip is feathered (FIG. 11c). When r1<0, there is no whip and rapid change (FIG. 11d). FIG. 12b: When (r2−r1) is small, the change in row direction is also rapid. It is smoothed when (r2−r1) is large (FIG. 12c). FIG. 12d: (r1<0) can be an option, but may reduce photon utilization rate, that is, increase image noise. FIG. 12e: small a may not be able to reduce the effect of extrapolation. FIG. 13: The center channel shows symmetric weighting, while (FIG. 12) shows asymmetric weight.

Figure 6:
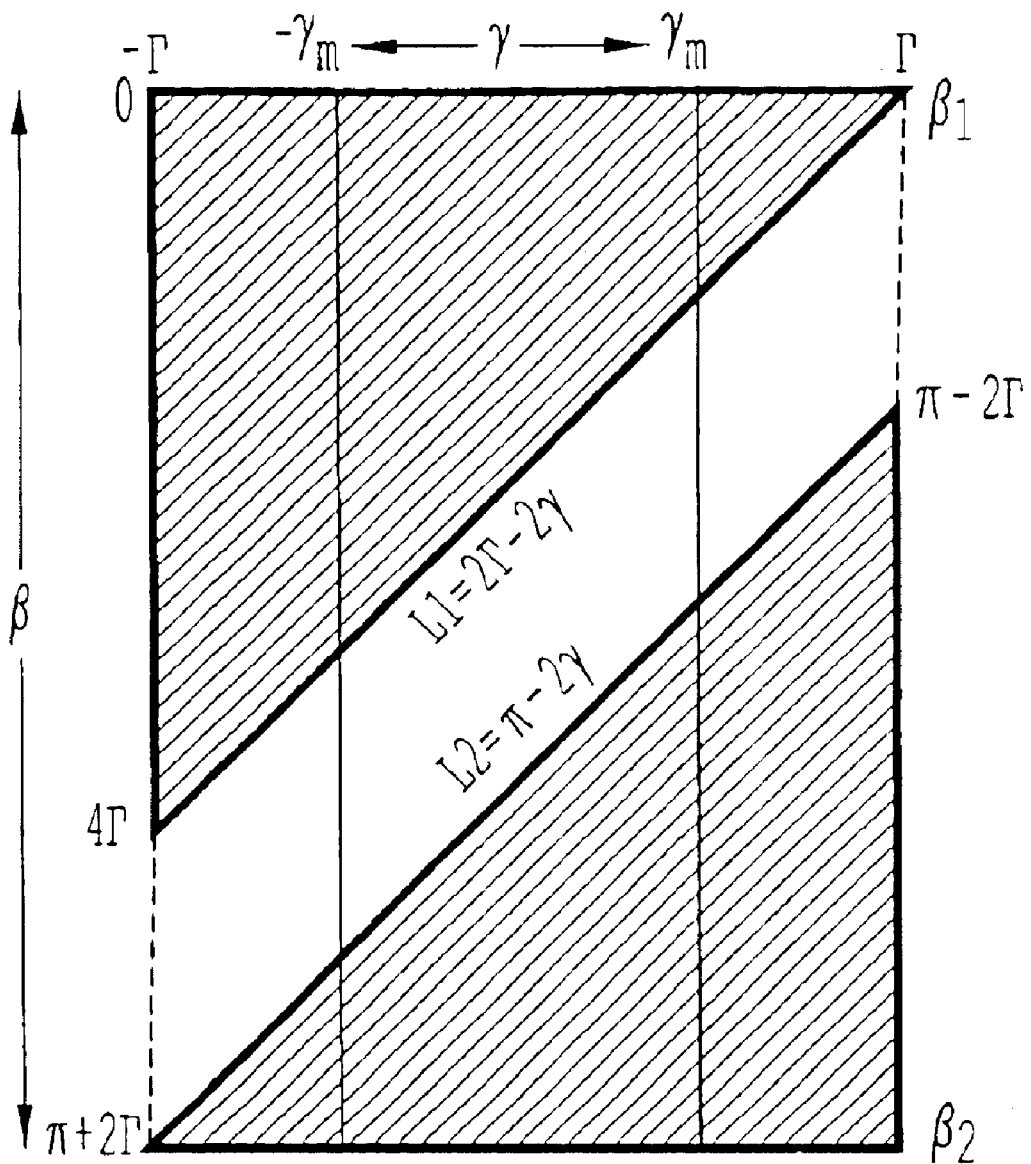
FIG. 6 depicts a weighting function for Extended Half-Scanning (MHS) applied to each segment of multiple views to be backprojected.
Figure 7:
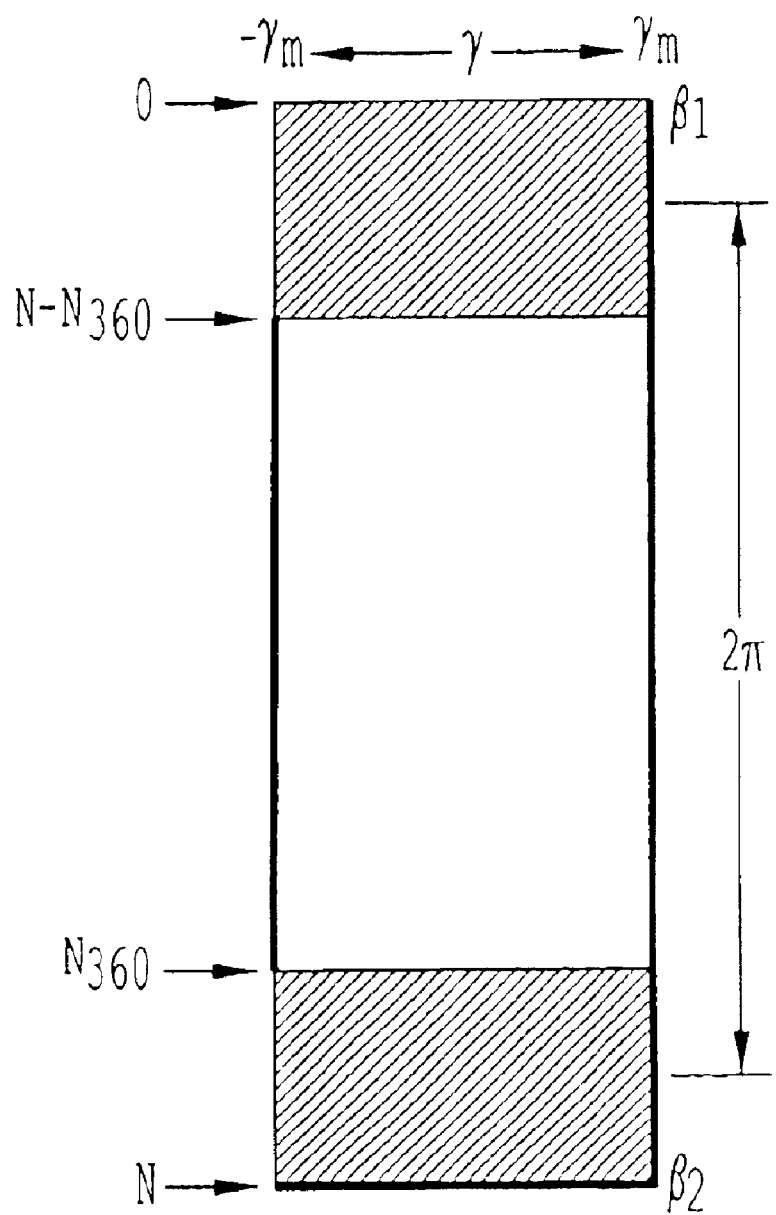
FIG. 7 represents a weighting function for overscanning (hereafter, OS).
Figure 16:
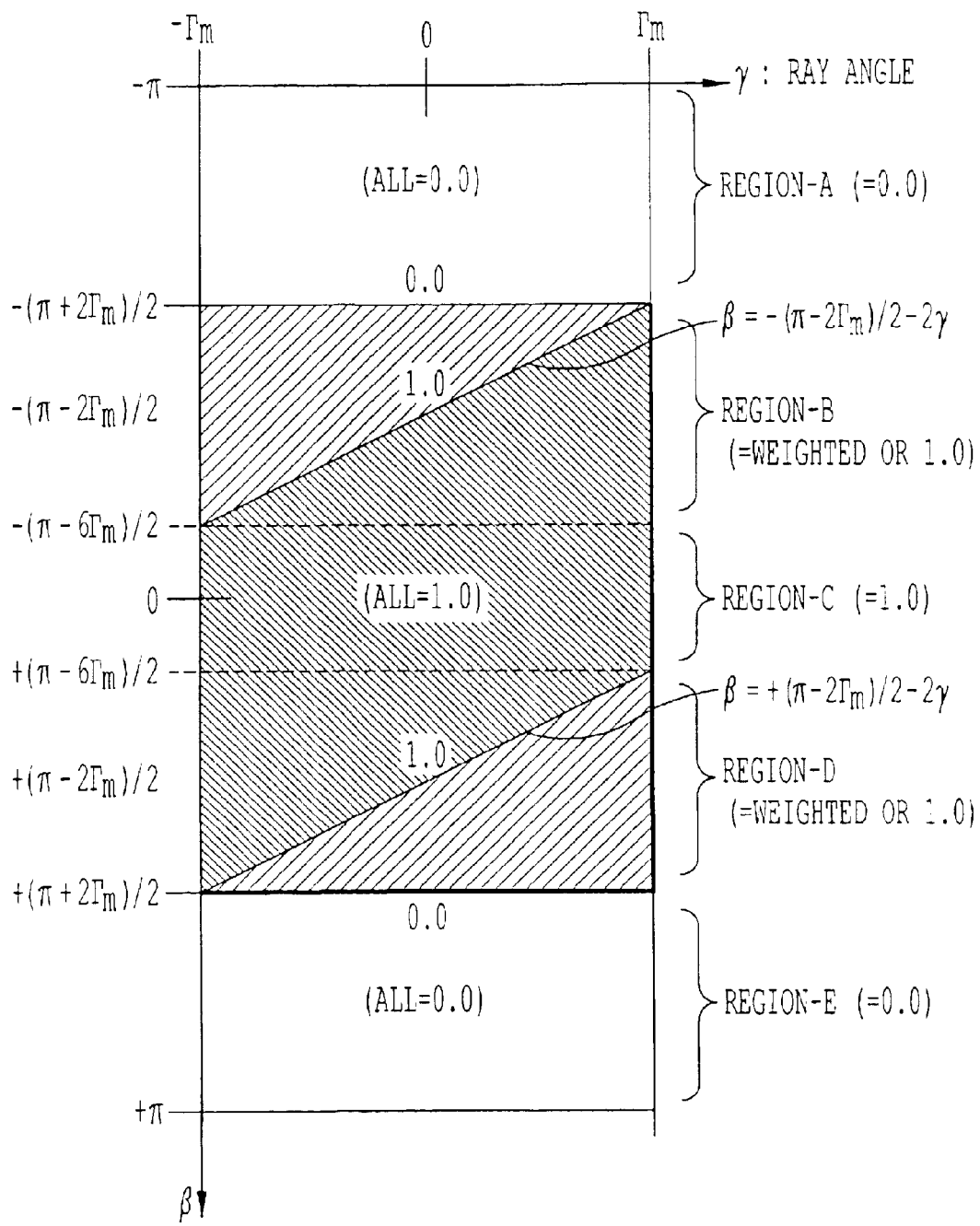
FIG. 16 illustrates a weighting function of MHS.
Figure 17A:
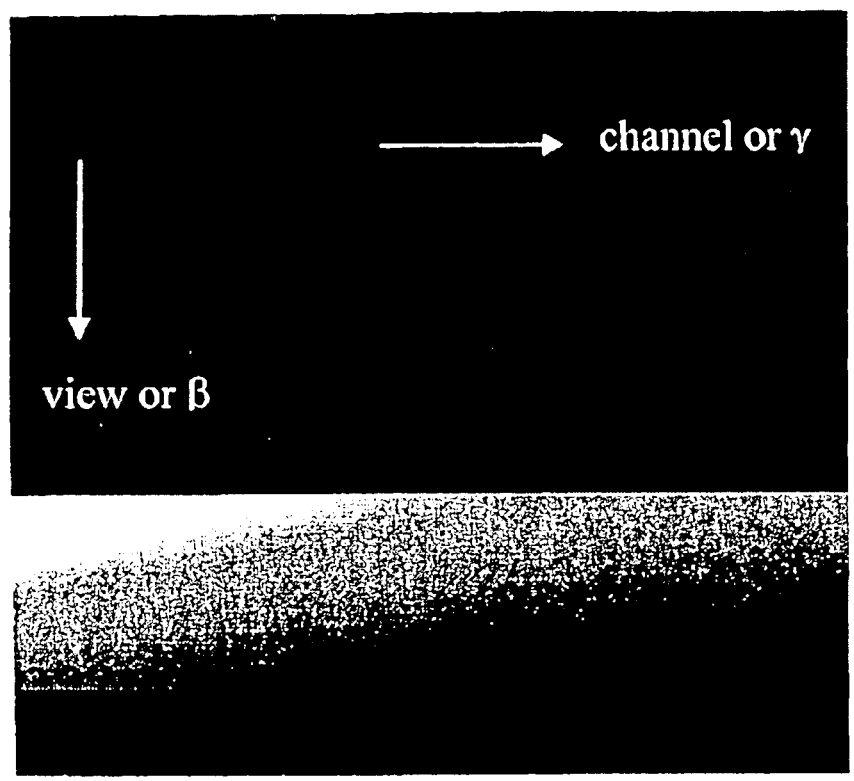
FIGS. 17a–17c, 18a–18e, and 19a–19e illustrate results using the current MHS method.
Figure 17B:
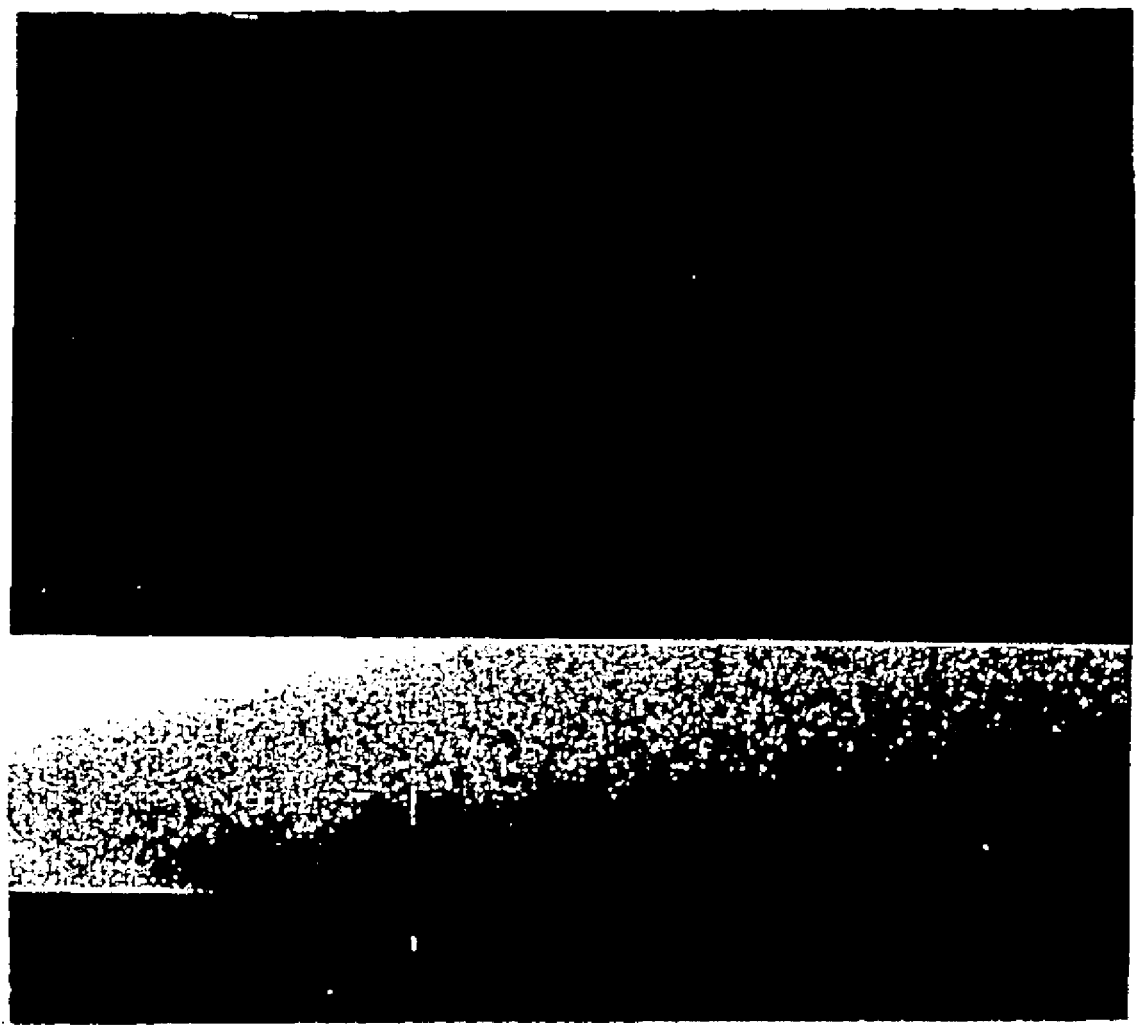
Figure 17C:
Figure 18A:
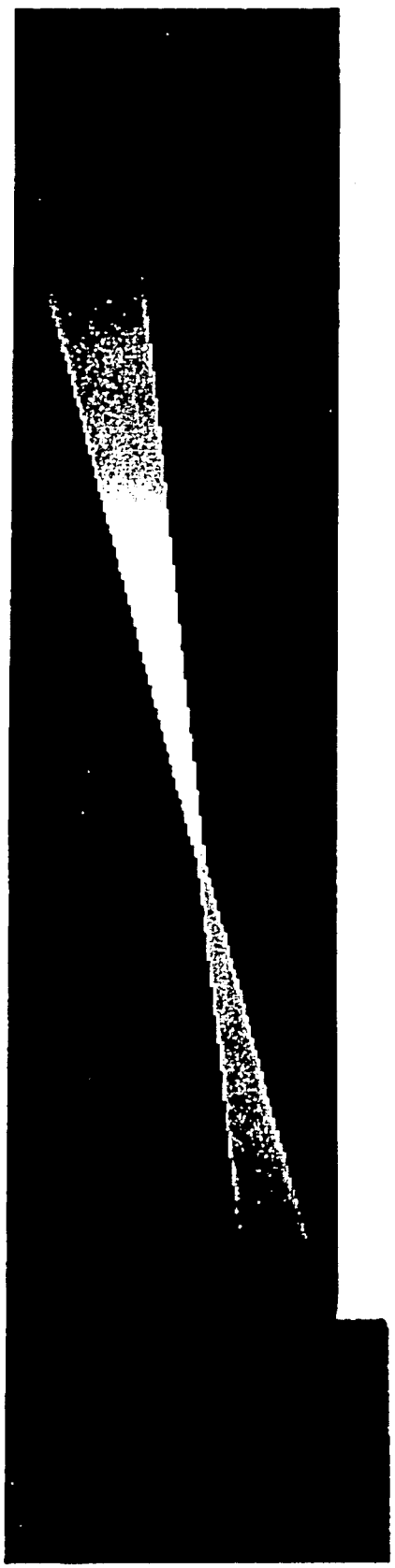
Figure 18B:
Figure 18C:
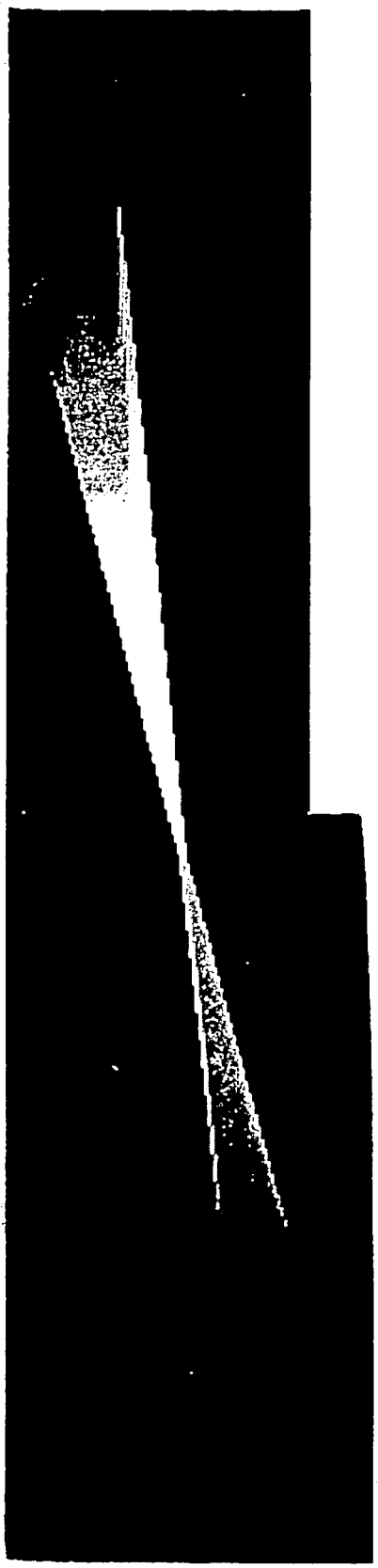
Figure 18D:
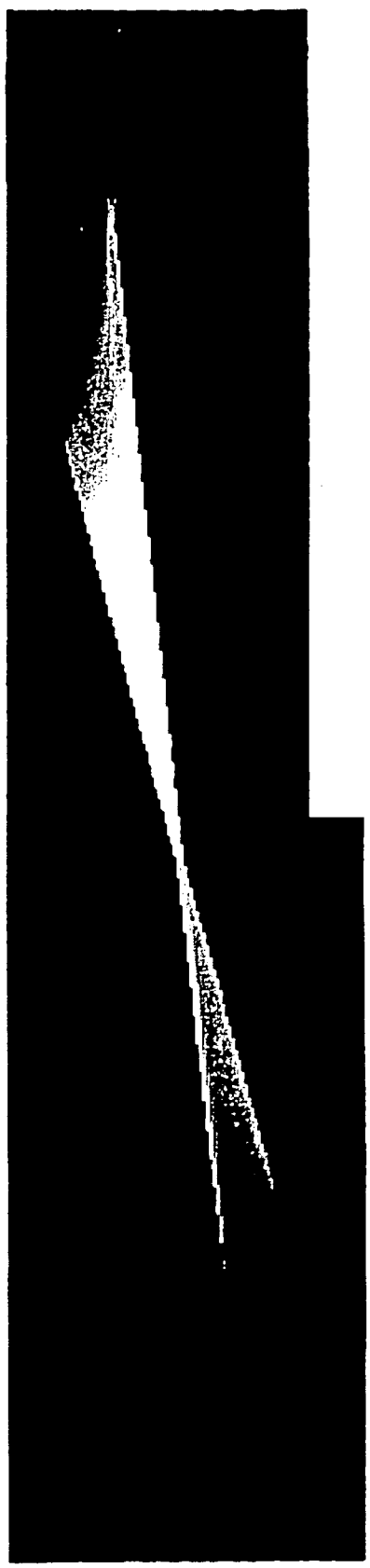
Figure 18E:
Figure 19A:
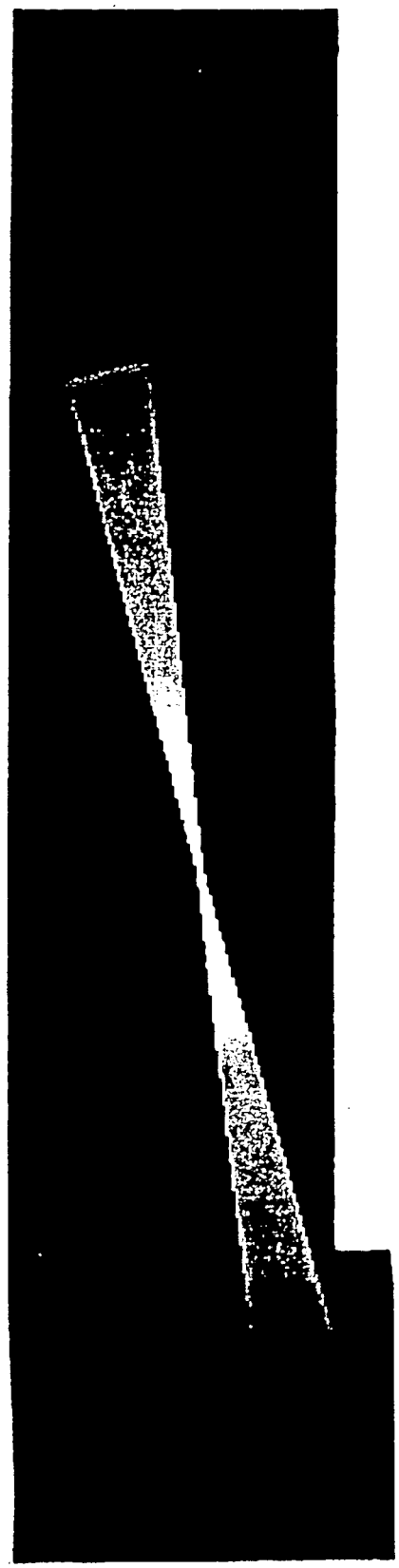
Figure 19B:
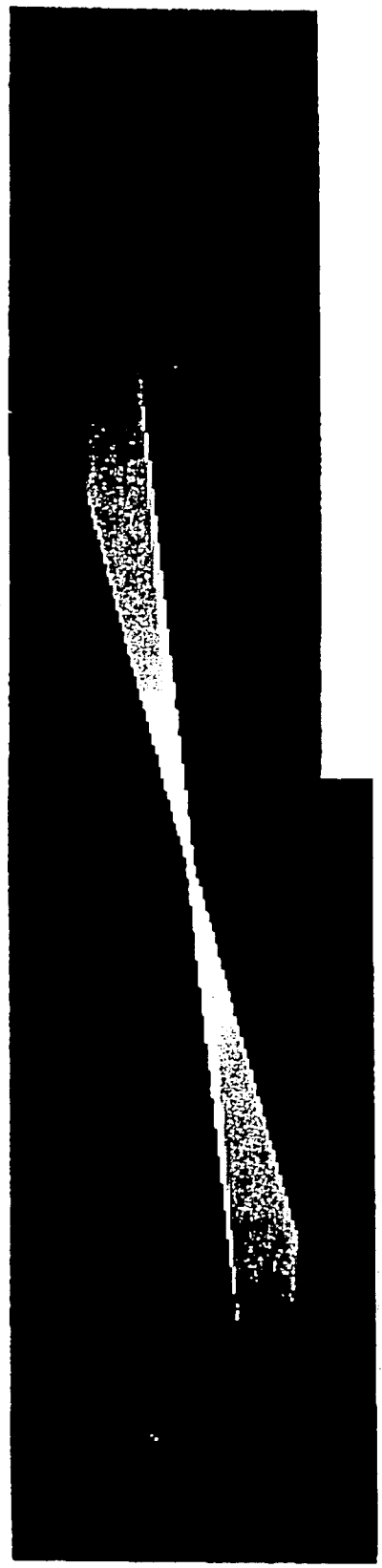
Figure 19C:
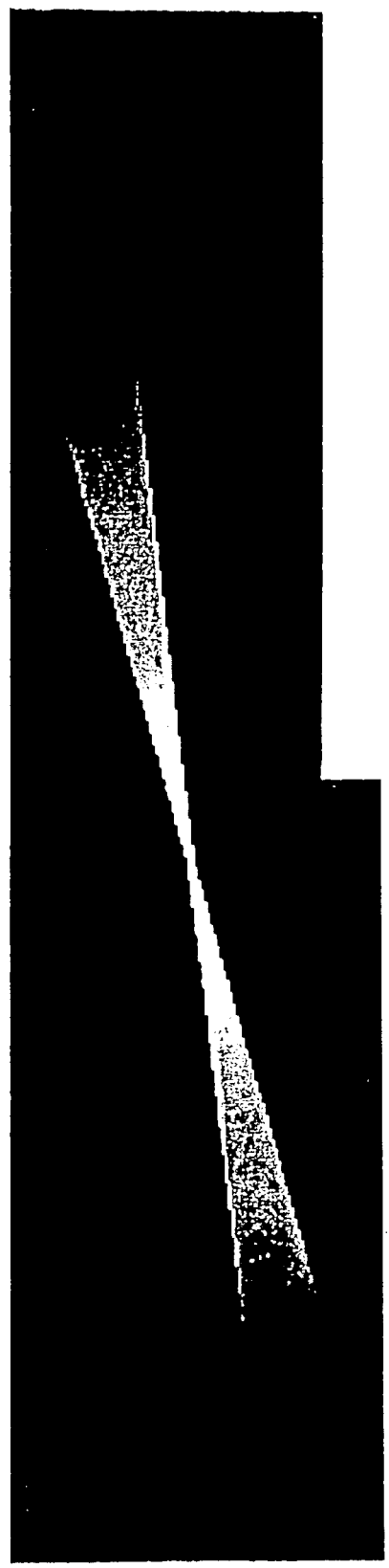
Figure 19D:
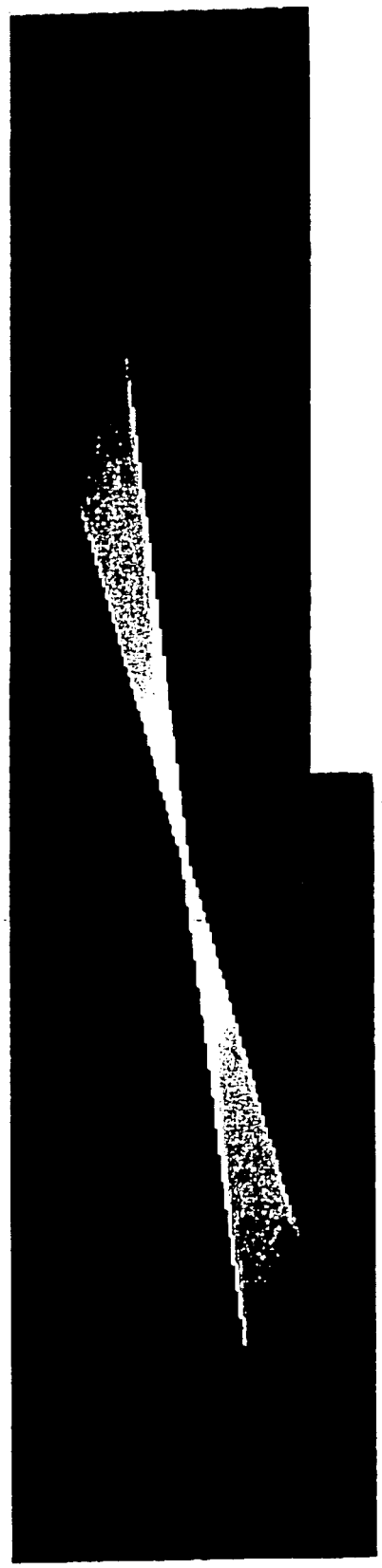
Figure 19E:
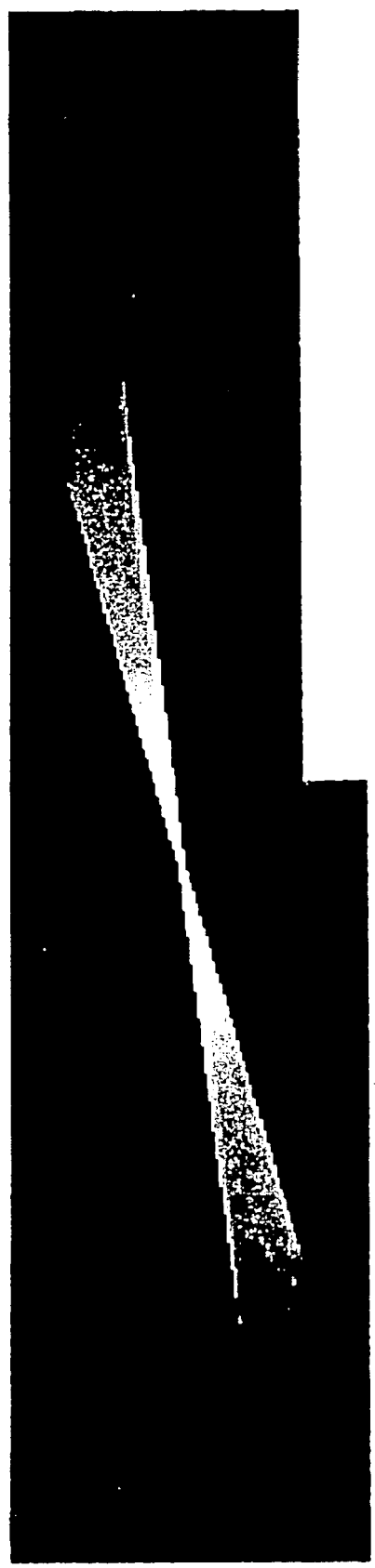

The first formula applied is for MHS weight $w_{p,\beta,\gamma}$ (independent of cone angle $\alpha$), as illustrated in FIG. 16, which is an alternative depiction of the MHS weight of FIG. 6. Below is a modified MHS weight when $\beta = [-(\pi+2\Gamma_m)/2, (\pi+2\Gamma_m)/2]$, rather than when $\beta = [0, \pi+2\Gamma_m]$. It is also possible to use a version for $\beta = [0, \pi+2\Gamma_m]$. As shown in FIG. 16, if $(\beta < -(\pi+2\Gamma_m)/2)$ then Region A applies and $$w_{p,\beta,\gamma} = 0 \quad (A1)$$

Else if $(-(\pi+2\Gamma_m)/2 \le \beta < -(\pi-6\Gamma_m)/2)$, Region B applies. If $$(\gamma < (-\frac{\pi}{2} - \Gamma_m - \beta)/2),$$

then the left side region: reversed triangle area applies.

$$x_{p,\beta,\gamma} = \left(\frac{\pi}{2} + \Gamma_m + \beta\right)/2(\Gamma_m - \gamma) \quad (A2)$$

$$w_{p,\beta,\gamma} = 3x_{p,\beta,\gamma}^2 - 2x_{p,\beta,\gamma}^3 \quad (A3)$$

Otherwise if $((\pi/2 - \Gamma_m - \beta)/2 \le \gamma)$, then the right side region: triangle (exists when $\Gamma_m > \pi/2 - 2\gamma_m$) applies and $$x_{p,\beta,\gamma} = \left(\frac{\pi}{2} + \Gamma_m - \beta\right)/2(\Gamma_m + \gamma) \quad (A4)$$

$$w_{p,\beta,\gamma} = 3x_{p,\beta,\gamma}^2 - 2x_{p,\beta,\gamma}^3 \quad (A5)$$

Else the center region: flat applies and $$w_{p,\beta,\gamma}=1. \quad (A6)$$

Else if $(-(\pi-6\Gamma_m)/2 \leq \beta < (\pi-6\Gamma_m)/2)$, then Region C applies and $$w_{p,\beta,\gamma}=1 \quad (A7)$$

Else if $((\pi-6\Gamma_m)/2 \leq \beta < (\pi+2\Gamma_m)/2)$, Region D applies and the left side of Region D is taken care of by Region B.
If $$\left(\left(\frac{\pi}{2} - \Gamma_m - \beta\right)/2 \leq \gamma\right)$$

then the right side region, triangle applies:

$$x_{p,\beta,\gamma} = \left(\frac{\pi}{2} + \Gamma_m - \beta\right)/2(\Gamma_m + \gamma) \quad (A8)$$

$$w_{p,\beta,\gamma} = 3x_{p,\beta,\gamma}^2 - 2x_{p,\beta,\gamma}^3 \quad (A9)$$

Else in the center region, flat:

$$w_{p,\beta,\gamma}=1 \quad (A10)$$

Else if $((\pi+2\Gamma_m)/2 \leq \beta)$, Region E applies:

$$w_{p,\beta,\gamma}=0 \quad (A11)$$

Obviously, numerous modifications and variations of the present invention are possible in light of the above teachings. It is therefore to be understood that within the scope of the appended claims, the invention may be practiced otherwise than as specifically described herein.

What is claimed is:

1. A method for obtaining data from a computed tomography (CT) scan, comprising:
    obtaining projection data from at least one detector row in a CT system;
    applying a weighting function including a cone-angle dependent weight corresponding to data validity to the projection data, thereby obtaining weighted data;
    filtering the weighted data; and
    backprojecting the weighted data taking cone-angle into account.

2. The method according to claim 1, wherein the backprojecting step includes applying Feldkamp reconstruction.

3. The method according to claim 1, wherein the weighting function includes an MHS function.

4. The method according to claim 1, wherein the weighting function includes an OS function.

5. An X-ray CT apparatus, comprising:
    a helical scanning device configured to collect projection data while at least one of a gantry and a couch moves along an axial direction of the couch, the helical scanning device including,
        an X-ray source configured to generate X-rays, and
        a detector having detector elements arranged in a plurality of rows along the axial direction and configured to produce the projection data; and
    a processor comprising,
        a weighting device configured to apply a weighting function including
        a cone-angle dependent weight corresponding to data validity to the projection data, thereby obtaining weighted data,
        a filtering device configured to filter the weighted data, and
        a backprojecting device configured to backproject the weighted data taking cone-angle into account.

6. The apparatus according to claim 5, wherein the backprojecting device is configured to perform Feldkamp reconstruction.

7. The apparatus according to claim 5, wherein the weighting function includes an MHS function.

8. The apparatus according to claim 5, wherein the weighting function includes an OS function.

9. An X-ray CT apparatus, comprising:
    a helical scanning device configured to collect projection data while at least one of a gantry and a couch moves along an axial direction of the couch, the helical scanning device including,
        an X-ray source configured to generate X-rays, and
        a detector having detector elements arranged in a plurality of rows along the axial direction and configured to produce the projection data; and
    a processor comprising,
        means for weighting that applies a weighting function including a cone-angle dependent weight corresponding to data validity to the projection data, thereby obtaining weighted data,
        a filtering device configured to filter the weighted data, and
        a backprojecting device configured to backproject the weighted data taking cone-angle into account.

10. The apparatus according to claim 9, wherein the means for backprojecting performs Feldkamp reconstruction.

11. The apparatus according to claim 9, wherein the weighting function includes an MHS function.

12. The apparatus according to claim 9, wherein the weighting function includes an OS function.

13. A method for processing data obtained from a CT scan, comprising:
    defining at least one parameter;
    calculating a first cone-angle for at least one detector row;
    storing the first cone-angle for the at least one detector row;
    calculating at least one OS weight for at least one direct ray and a plurality of complementary rays;
    determining a value of the at least one OS weight;
    calculating a second cone-angle for the plurality of complementary rays;
    calculating at least one row dependent weight;
    calculating a normalized weight based on the at least one row dependent weight, thereby obtaining the normalized weight for use in backprojection, wherein
    the calculating a second cone-angle is performed with a limitation to avoid extraordinary cases.

14. The method of claim 13, wherein the method further comprises obtaining a number of valid complementary rays before determining a value of the at least one OS weight.

15. The method of claim 14, wherein a number of the plurality of complementary rays is two to four.

16. The method of claim 13, wherein a number of the plurality of complementary rays is six or more.

17. A computer program product storing instructions for execution on a computer system, which when executed by the computer system, causes the computer system to perform the method recited in any one of claims 1–4 13, and 14–16.

18. A method for obtaining data from a computed tomography (CT) scan, comprising:

obtaining projection data from at least one detector row in a CT system;

applying a weighting function including a cone-angle dependent weight to the projection data, the weight on a region of measured data being larger than the weight on an outside region of measured data, thereby obtaining weighted data; and reconstructing a tomography image based on the weighted data taking cone-angle into account.

19. An X-ray CT apparatus, comprising:

a helical scanning device configured to collect projection data while at least one of a gantry and a couch moves along an axial direction of the couch, the helical scanning device including, an X-ray source configured to generate X-rays, and a detector having detector elements arranged in a plurality of rows along the axial direction and configured to produce the projection data; and a processor comprising, means for weighting that applies a weighting function including a cone-angle dependent weight to the projection data, the weight on a region of measured data being larger than the weight on an outside region of measured data, thereby obtaining weighted data, a filtering device configured to filter the weighted data, and a backprojecting device configured to backproject the weighted data taking cone-angle into account.

* * * * *